United States Patent
Stoddart et al.

(10) Patent No.: US 12,172,964 B2
(45) Date of Patent: Dec. 24, 2024

(54) TRICYCLIC OCTACATIONIC CYCLOPHANE AND ITS USE IN COMPLEXATION WITH PERLENE DIIMIDE DYES

(71) Applicant: Northwestern University, Evanston, IL (US)

(72) Inventors: James Fraser Stoddart, Evanston, IL (US); Wenqi Liu, Evanston, IL (US)

(73) Assignee: Northwestern University, Evanston, IL (US)

( * ) Notice: Subject to any disclaimer, the term of this patent is extended or adjusted under 35 U.S.C. 154(b) by 486 days.

(21) Appl. No.: 17/445,053

(22) Filed: Aug. 13, 2021

(65) Prior Publication Data

US 2022/0048860 A1 Feb. 17, 2022

Related U.S. Application Data

(60) Provisional application No. 63/065,181, filed on Aug. 13, 2020.

(51) Int. Cl.
| | |
|---|---|
| *C07D 213/22* | (2006.01) |
| *C09B 67/48* | (2006.01) |
| *C09B 69/10* | (2006.01) |
| *G01N 21/64* | (2006.01) |

(52) U.S. Cl.
CPC ........ *C07D 213/22* (2013.01); *C09B 67/0025* (2013.01); *C09B 69/109* (2013.01); *G01N 21/6428* (2013.01); *G01N 21/6458* (2013.01); *G01N 2021/6417* (2013.01); *G01N 2021/6439* (2013.01)

(58) Field of Classification Search
CPC . C07D 213/22; C09B 67/0025; C09B 69/109; G01N 21/6428; G01N 21/6458; G01N 2021/6417; G01N 2021/6439
See application file for complete search history.

(56) References Cited

U.S. PATENT DOCUMENTS 8,273,875 B2  9/2012  Smith et al.

OTHER PUBLICATIONS

Liu, J Am Chem Soc, Feb. 2020, 142, 3163173. (Year: 2020).*
Natarajan, Crystal Growth & Design, vol. 5(1), 2005, 69-72. (Year: 2005).*
Ariga, K.; Li, J.; Fei, J.; Ji, Q.; Hill, J. P. Nanoarchitectonics for Dynamic Functional Materials from Atomic-/Molecular-Level Manipulation to Macroscopic Action. Adv. Mater. 2016, 28, 1251-1286.
Assaf, K. I.; Nau, W. M. Cucurbiturils: From Synthesis to High-Affinity Binding and Catalysis. Chem. Soc. Rev. 2015, 44, 394-418.
Barnes, J. C.; Juríček, M.; Strutt, N. L.; Frasconi, M.; Sampath, S.; Giesener, M. A.; McGrier, P. L.; Bruns, C. J.; Stern, C. L.; Sarjeant, A. A.; et al. ExBox: A Polycyclic Aromatic Hydrocarbon Scavenger. J. Am. Chem. Soc. 2013, 135, 183-192.
Barnes, J. C .; Juríček, M.; Vermeulen, N. A.; Dale, E. J.; Stoddart, J. F. Synthesis of ExnBox Cyclophanes. J. Org. Chem. 2013, 78, 11962-11969.
Barrow, S. J.; Kasera, S.; Rowland, M. J.; Del Barrio, J.; Scherman, O. A. Cucurbituril-Based Molecular Recognition. Chem. Rev. 2015, 115, 12320-12406.
Biedermann, F.; Elmalem, E.; Ghosh, I.; Nau, W. M.; Scherman, O. A. Strongly Fluorescent, Switchable Perylene Bis (Diimide) Host-Guest Complexes with Cucurbit[8]uril in Water. Angew. Chem. Int. Ed. 2012, 51, 7739-7743.
Biedermann, F.; Nau, W. M.; Schneider, H. J. The Hydrophobic Effect Revisited—Studies with Supramolecular Complexes Imply High-Energy Water as a Noncovalent Driving Force. Angew. Chem. Int. Ed. 2014, 53, 11158-11171.
Brouwer, A.M. Standards for Photoluminescence Quantum Yield Measurements in Solution (IUPAC Technical Report). Pure Appl. Chem. 2011, 83, 2213-2228.
Butkevich, A. N.; Lukinavičius, G.; D'Este, E.; Hell, S. W. Cell-Permeant Large Stokes Shift Dyes for Transfection-Free Multicolor Nanoscopy. J. Am. Chem. Soc. 2017, 139, 12378-12381.
Cao, L.; Sekutor, M.; Zavalij, P. Y.; Mlinaric-Majerski, K.; Glaser, R.; Isaacs, L. Cucurbit[7]uril. Guest Pair with an Attomolar Dissociation Constant. Angew. Chem., Int. Ed. 2014, 53, 988-993.
Chodera, J. D.; Mobley, D. L. Entropy-Enthalpy Compensation: Role and Ramifications in Biomolecular Ligand Recognition and Design. Annu. Rev. Biophys. 2013, 42, 121-142.
Chu, J.; Oh, Y.; Sens, A.; Ataie, N.; Dana, H.; Macklin, J. J.; Laviv, T.; Welf, E. S.; Dean, K. M.; Zhang, F.; et al. A Bright Cyan-Excitable Orange Fluorescent Protein Facilitates Dual-Emission Microscopy and Enhances Bioluminescence Imaging in Vivo. Nat. Biotechnol. 2016, 34, 760-767.
Cremer, P. S.; Flood, A. H.; Gibb, B. C.; Mobley, D. L. Collaborative Routes to Clarifying the Murky Waters of Aqueous Supramolecular Chemistry. Nat. Chem. 2017, 10, 8-16.
Dale, E. J.; Vermeulen, N. A.; Juríček, M.; Barnes, J. C.; Young, R. M.; Wasielewski, M. R.; Stoddart, J. F. Supramolecular Explorations: Exhibiting The Extent of Extended Cationic Cyclophanes. Acc. Chem. Res. 2016, 49, 262-273.
Dale, E. J.; Vermeulen, N. A.; Thomas, A. A.; Barnes, J. C.; Juríček, M.; Blackburn, A. K.; Strutt, N. L.; Sarjeant, A. A.; Stern, C. L.; Denmark, S. E.; et al. ExCage. J. Am. Chem. Soc. 2014, 136, 10669-10682.
Deutman, A. B. C.; Monnereau, C.; Elemans, J. a a W.; Ercolani, G.; Nolte, R. J. M.; Rowan, A. E. Mechanism of Threading a Polymer through a Macrocyclic Ring. Science. 2008, 322, 1668-1671.
Dolomanov, O. V, Bourhis, L.J., Gildea, R.J., Howard, J.A.K., and Puschmann, H. OLEX2: A Complete Structure Solution, Refinement and Analysis Program. J. Appl. Crystallogr. 2009, 42, 339-341.
Fan, J.; Hu, M.; Zhan, P.; Peng, X. Energy Transfer Cassettes Based on Organic Fluorophores: Construction and Applications in Ratiometric Sensing. Chem. Soc. Rev. 2013, 42, 29-43.
Garwin, S. A.; Kelley, M. S. J.; Sue, A. C.; Que, E. L.; Schatz, G. C.; Woodruff, T. K.; O'Halloran, T. V. Interrogating Intracellular Zinc Chemistry with a Long Stokes Shift Zinc Probe ZincBY-4. J. Am. Chem. Soc. 2019, 141, 16696-16705.

(Continued)

*Primary Examiner* — D Margaret M Seaman
(74) *Attorney, Agent, or Firm* — Quarles & Brady LLP

(57) ABSTRACT

Disclosed herein is a tricyclic octacationic cyclophane and complexes comprising the tricyclic octacationic cyclophane and a perylene diimide dye complexed therein and methods of using and making the cyclophane and complexes.

11 Claims, 15 Drawing Sheets

(56) References Cited

OTHER PUBLICATIONS

Gibb, B. C. Supramolecular Assembly and Binding in Aqueous Solution: Useful Tips Regarding the Hofmeister and Hydrophobic Effects. Isr. J. Chem. 2011, 51, 798-806.

Hargrove, A.E., Zhong, Z., Sessler, J.L., and Anslyn, E. V. Algorithms for the Determination of Binding Constants and Enantiomeric Excess in Complex Host: Guest Equilibria Using Optical Measurements. New J. Chem. 2010, 34, 348-354.

Heek, T.; Fasting, C.; Rest, C.; Zhang, X.; Würthner, F.; Haag, R. Highly Fluorescent Water-Soluble Polyglycerol-Dendronized Perylene Bisimide Dyes. Chem. Commun. 2010, 46, 1884-1886.

Heinzmann, C.; Weder, C.; de Espinosa, L. M. Supramolecular Polymer Adhesives: Advanced Materials Inspired by Nature. Chem. Soc. Rev. 2015, 342, 342-358.

Houk, K. N.; Leach, A. G.; Kim, S. P.; Zhang, X. Binding Affinities of Host-Guest, Protein-Ligand, and Protein-Transition-state Complexes. Angew. Chem. Int. Ed. 2003, 42, 4872-4897.

Ishida, T.; Morisaki, Y.; Chujo, Y. Synthesis of Covalently Bonded Nanostructure from Two Porphyrin Molecular Wires Leading to a Molecular Tube. Tetrahedron Lett. 2006, 47, 5265-5268.

Jiao, Y., Liu, K., Wang, G., Wang, Y., and Zhang, X. Supramolecular Free Radicals: Near-Infrared Organic Materials with Enhanced Photothermal Conversion. Chem. Sci. 2015, 6, 3975-3980.

Jono, K.; Suzuki, A.; Akita, M.; Albrecht, K.; Yamamoto, K.; Yoshizawa, M. A Polyaromatic Molecular Clip That Enables the Binding of Planar, Tubular, and Dendritic Compounds. Angew. Chem. Int. Ed. 2017, 56, 3570-3574.

Kogure, T.; Karasawa, S.; Araki, T.; Saito, K.; Kinjo, M.; Miyawaki, A. A Fluorescent Variant of a Protein from The Stony Coral Montipora Facilitates Dual-Color Single-Laser Fluorescence Cross-Correlation Spectroscopy. Nat. Biotechnol. 2006, 24, 577-581.

Lefebvre, C.; Rubez, G.; Khartabil, H.; Boisson, J. C.; Contreras-García, J.; Hénon, E. Accurately Extracting the Signature of Intermolecular Interactions Present in the NCI Plot of the Reduced Density Gradient Versus Electron Density. Phys. Chem. Chem. Phys. 2017, 19, 17928-17936.

Li, D.-H.; Smith, B. D. Molecular Recognition Using Tetralactam Macrocycles with Parallel Aromatic Sidewalls. Beilstein J. Org. Chem. 2019, 15, 1086-1095.

Li, X.; Hihath, J.; Chen, F.; Masuda, T.; Zang, L.; Tao, N. Thermally Activated Electron Transport in Single Redox Molecules. J. Am. Chem. Soc. 2007, 129, 11535-11542.

Liu, W.; Johnson, A.; Smith, B. D. Guest Back-Folding: A Molecular Design Strategy That Produces a Deep-Red Fluorescent Host/Guest Pair with Picomolar Affinity in Water. J. Am. Chem. Soc. 2018, 140, 3361-3370.

Liu, W.; Samanta, S. K.; Smith, B. D.; Isaacs, L. Synthetic Mimics of Biotin/(Strept)Avidin. Chem. Soc. Rev. 2017, 46, 2391-2403.

Liu, Y.; Zhao, W.; Chen, C.-H.; Flood, A. H. Chloride Capture Using a C—H Hydrogen Bonding Cage. Science. 2019, 365, 159-161.

Lu, T .; Chen, F. Multiwfn: A Multifunctional Wavefunction Analyzer. J. Comput. Chem. 2012, 33, 580-592.

Mako, T. L.; Racicot, J. M.; Levine, M. Supramolecular Luminescent Sensors. Chem. Rev. 2019, 119, 322-477.

Murray, J.; Kim, K.; Ogoshi, T.; Yao, W.; Gibb, B. C. The Aqueous Supramolecular Chemistry of Cucurbit[n]urils, Pillar [n]Arenes and Deep-Cavity Cavitands. Chem. Soc. Rev. 2017, 46, 2479-2496.

Nau, W. M.; Florea, M.; Assaf, K. I. Deep Inside Cucurbiturils: Physical Properties and Volumes of Their Inner Cavity Determine the Hydrophobic Driving Force for Host-Guest Complexation. Isr. J. Chem. 2011, 51, 559-577.

Ogoshi, T.; Yamagishi, T. A.; Nakamoto, Y. Pillar-Shaped Macrocyclic Hosts Pillar[n]arenes: New Key Players for Supramolecular Chemistry. Chem.Rev 2016, 116, 7937-8002.

Pan, J.; Chen, W.; Ma, Y.; Pan, G. Molecularly Imprinted Polymers as Receptor Mimics for Selective Cell Recognition. Chem. Soc. Rev. 2018, 47, 5574-5587.

Persch, E.; Dumele, O.; Diederich, F. Molecular Recognition in Chemical and Biological Systems. Angew. Chem. Int. Ed. 2015, 54, 3290-3327.

Pettersen, E.F., Goddard, T.D., Huang, C.C., Couch, G.S., Greenblatt, D.M., Meng, E.C., and Ferrin, T.E. UCSF Chimera—A Visualization System for Exploratory Research and Analysis. J. Comput. Chem. 2004, 25, 1605-1612.

Rekharsky, M. V; Mori, T.; Yang, C.; Ko, Y. H.; Selvapalam, N.; Kim, H.; Sobransingh, D.; Kaifer, A. E.; Liu, S.; Isaacs, L.; et al. A Synthetic Host-Guest System Achieves Avidin-Biotin Affinity by Overcoming Enthalpy-Entropy Compensation. Proc. Natl. Acad. Sci. U. S. A. 2007, 104, 20737-20742.

Ringe, D.; Petsko, G. A. How Enzymes Work. Science. 2008, 320, 1428-1429.

Ryan, S. T. J.; Young, R. M.; Henkelis, J. J.; Hafezi, N.; Vermeulen, N. A.; Hennig, A.; Dale, E. J.; Wu, Y.; Krzyaniak, M. D.; Fox, A.; et al. Energy and Electron Transfer Dynamics within a Series of Perylene Diimide/Cyclophane Systems. J. Am. Chem. Soc. 2015, 137, 15299-15307.

Ryan, S.T.J., Del Barrio, J., Ghosh, I., Biedermann, F., Lazar, A.I., Lan, Y., Coulston, R.J., Nau, W.M., and Scherman, O.A.. Efficient Host-Guest Energy Transfer in Polycationic Cyclophane-Perylene Diimide Complexes in Water. J. Am. Chem. Soc. 2014, 136, 9053-9060.

Sapotta, M.; Hofmann, A.; Bialas, D.; Würthner, F. A Water-Soluble Perylene Bisimide Cyclophane as a Molecular Probe for the Recognition of Aromatic Alkaloids. Angew. Chem. Int. Ed. 2019, 58, 3516-3520.

Sarikaya, M.; Tamerler, C.; Jen, A. K.-Y.; Schulten, K.; Baneyx, F. Molecular Biomimetics: Nanotechnology through Biology. Nat. Mater. 2003, 2, 577-585.

Schneider, C.A., Rasband, W.S., and Eliceiri, K.W. NIH Image to ImageJ: 25 Years of Image Analysis. Nat. Methods 2012, 9, 671-675.

Schreiber, C. L.; Smith, B. D. Molecular Conjugation Using Non-Covalent Click Chemistry. Nat. Rev. Chem. 2019, 3, 393-400.

Sednev, M. V.; Belov, V. N.; Hell, S. W. Fluorescent Dyes with Large Stokes Shifts for Super-Resolution Optical Microscopy of Biological Objects: A Review. Methods Appl. Fluoresc. 2015, 3, Apr. 2004.

Sheldrick, G.M. A Short History of SHELX. Acta Crystallogr. Sect. A. 2008, 64, 112-122.

Sheldrick, G.M. SHELXT-Integrated Space-Group and Crystal-Structure Determination. Acta Crystallogr. Sect. A. 2015, 71, 3-8.

Shetty, D.; Khedkar, J. K.; Park, K. M.; Kim, K. Can We Beat The Biotin-Avidin Pair?: Cucurbit[7]uril-Based Ultrahigh Affinity Host-Guest Complexes and Their Applications. Chem. Soc. Rev. 2015, 44, 8747-8761.

Spenst, P.; Würthner, F. A Perylene Bisimide Cyclophane as a "Turn-On" and "Turn-Off" Fluorescence Probe. Angew. Chem. Int. Ed. 2015, 54, 10165-10168.

Sun, M.; Müllen, K.; Yin, M. Water-Soluble Perylenediimides: Design Concepts and Biological Applications. Chem. Soc. Rev. 2016, 45, 1513-1528.

Szwajkajzer, D.; Carey, J. Molecular and Biological Constraints on Ligand-Binding Affinity and Specificity. Biopolymers 1997, 44, 181-198.

Thordarson, P. Determining Association Constants from Titration Experiments in Supramolecular Chemistry. Chem. Soc. Rev. 2011, 40, 1305-23.

Thorn, A., Dittrich, B., and Sheldrick, G.M. Enhanced Rigid-Bond Restraints. Acta Crystallogr. Sect. A. 2012, 68, 448-451.

Tromans, R. A.; Carter, T. S.; Chabanne, L.; Crump, M. P.; Li, H.; Matlock, J. V.; Orchard, M. G.; Davis, A. P. A Biomimetic Receptor for Glucose. Nat. Chem. 2019, 11, 52-56.

Tsutsui, T.; Kusaba, S.; Yamashina, M.; Akita, M.; Yoshizawa, M. Open Versus Closed Polyaromatic Nanocavity: Enhanced Host Abilities toward Large Dyes and Pigments. Chem. Eur. J. 2019, 25, 4320-4324.

Wang, H.; Ji, X.; Li, Z.; Huang, F. Fluorescent Supramolecular Polymeric Materials. Adv. Mater. 2017, 29, 1606117.

Webber, M. J.; Langer, R. Drug Delivery by Supramolecular Design. Chem. Soc. Rev. 2017, 46, 6600-6620.

(56) References Cited

OTHER PUBLICATIONS

Weil, T.; Vosch, T.; Hofkens, J.; Peneva, K.; Müllen, K. The Rylene Colorant Family-Tailored Nanoemitters for Photonics Research and Applications. Angew. Chem. Int. Ed. 2010, 49, 9068-9093.

Würthner, F.; Saha-Möller, C. R.; Fimmel, B.; Ogi, S.; Leowanawat, P.; Schmidt, D. Perylene Bisimide Dye Assemblies as Archetype Functional Supramolecular Materials. Chem. Rev. 2016, 116, 962-1052.

Xin, N.; Guan, J.; Zhou, C.; Chen, X.; Gu, C.; Li, Y.; Ratner, M. A.; Nitzan, A.; Stoddart, J. F.; Guo, X. Concepts in The Design and Engineering of Single-Molecule Electronic Devices. Nat. Rev. Phys. 2019, 1, 211-230.

Xu, B.; Xiao, X.; Yang, X.; Zang, L.; Tao, N. Large Gate Modulation in The Current of a Room Temperature Single Molecule Transistor. J. Am. Chem. Soc. 2005, 127, 2386-2387.

Yamashina, M.; Kusaba, S.; Akita, M.; Kikuchi, T.; Yoshizawa, M. Cramming Versus Threading of Long Amphiphilic Oligomers into a Polyaromatic Capsule. Nat. Commun. 2018, 9, 3-9.

Yamashina, M.; Tsutsui, T.; Sei, Y.; Akita, M.; Yoshizawa, M. A Polyaromatic Receptor with High Androgen Affinity. Sci. Adv. 2019, 5, 1-8.

Yamauchi, Y.; Yoshizawa, M.; Akita, M.; Fujita, M. Engineering Double to Quintuple Stacks of a Polarized Aromatic in Confined Cavities. J. Am. Chem. Soc. 2010, 132, 960-966.

Yoshizawa, M.; Catti, L. Bent Anthracene Dimers as Versatile Building Blocks for Supramolecular Capsules. Acc. Chem. Res. 2019, 52, 2392-2404.

Yang, S.K.; Shi, X.; Park, S.; Doganay, S.; Ha, T.; Zimmerman, S.C. Monovalent, Clickable, Uncharged, Water-Soluble Perylenediimide-Cored Dendrimers for Target-Specific Fluorescent Biolabeling. J. Am. Chem. Soc. 2011, 133, 9964-9967.

\* cited by examiner

| | R |
|---|---|
| PDI1 | $CH_2CH_2NMe_2$ |
| PDI2 | $CH_2CH_2[OCH_2CH_2]_{44}OMe$ |

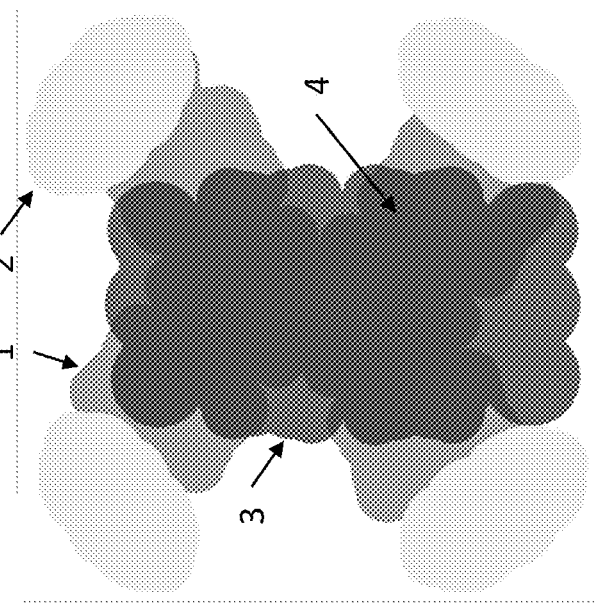
FIG. 3C
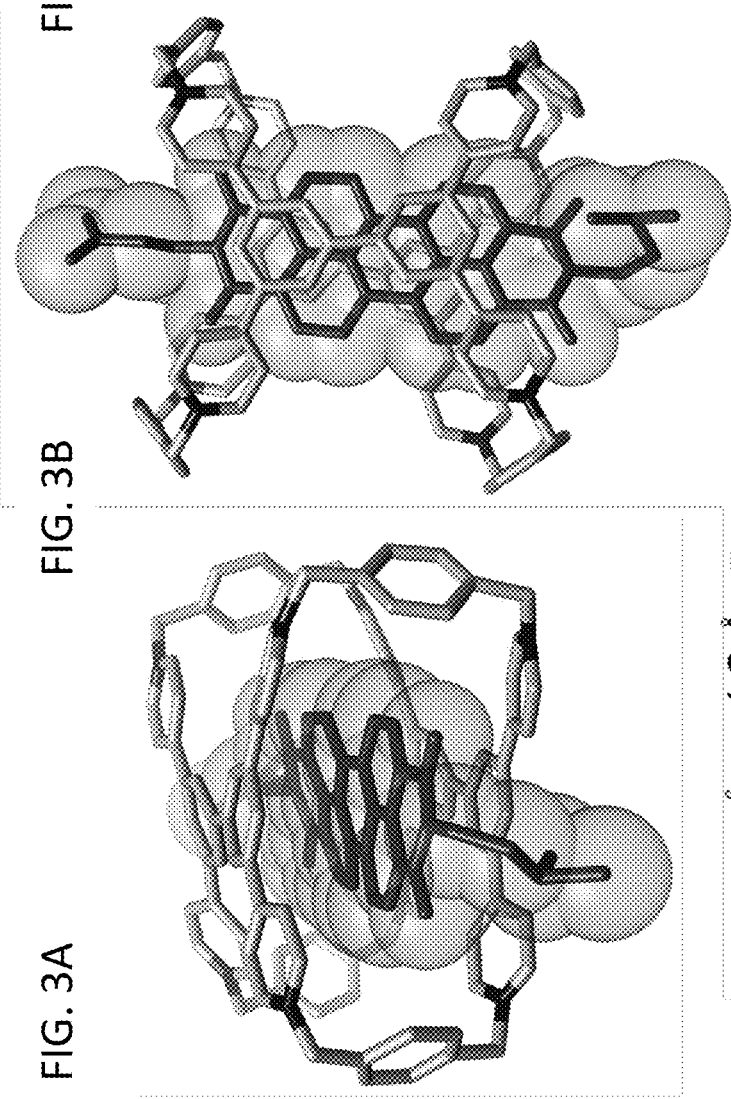
FIG. 3B
FIG. 3A
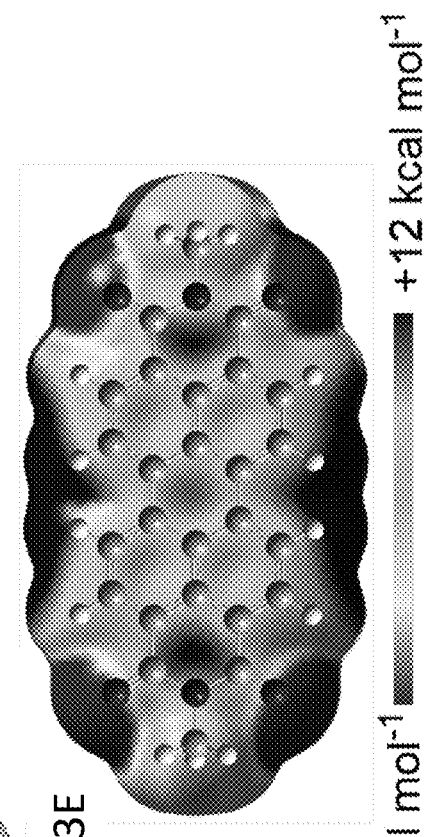
FIG. 3E
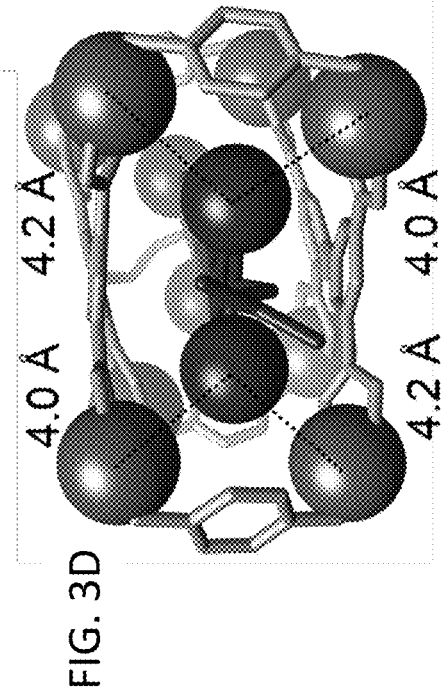
FIG. 3D FIG. 13
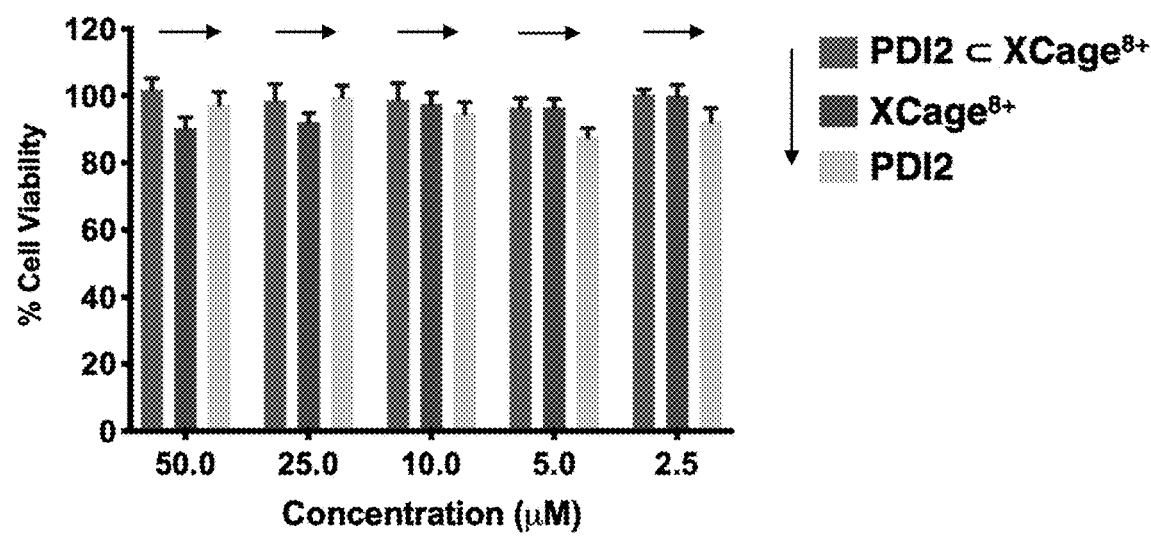
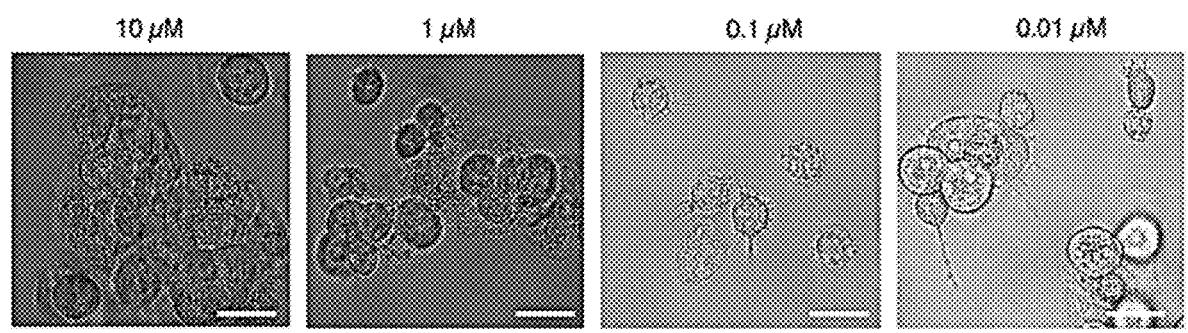
FIG. 14

TRICYCLIC OCTACATIONIC CYCLOPHANE AND ITS USE IN COMPLEXATION WITH PERLENE DIIMIDE DYES

CROSS-REFERENCE TO RELATED APPLICATIONS

This application claims benefit of priority to U.S. Patent Application Ser. No. 63/065,181, filed Aug. 13, 2020, the contents of which is incorporated by reference in its entirety.

BACKGROUND OF THE INVENTION

The rational design of wholly synthetic receptors that bind dye substrates with ultrahigh affinities is a challenging goal, especially in water. One of the grand challenges in supramolecular chemistry is to develop synthetic receptors with ultrahigh affinities, especially in water.[3-5] The majority of synthetic receptors described in the literature show[6] micromolar affinity or weaker binding. To date, examples of water compatible high-affinity receptors are rare and mainly limited to cucurbit[n]urils,[7-9] with a sparse distribution of them in pillararenes[10] and tetralactam macrocycles[11]. As a result, there exists a need to develop synthetic receptors that bind dye substrates for use in aqueous environments for live-cell imaging and the like.

BRIEF SUMMARY OF THE INVENTION

Disclosed herein is a tricyclic octacationic cyclophane, which exhibits complementary stereoelectronic binding towards perylene diimide dyes with picomolar affinity in water. The tricyclic octacationic cyclophane, or a salt thereof, may comprise a roof, a floor, and four pillars, wherein each of the roof and the floor are composed of a biphenyl unit having four pyridinium units extending therefrom and wherein each of the four pyridinium units of the roof are linked to another pyridinium unit of the floor by one of the four pillars. In some embodiments, the cyclophane is

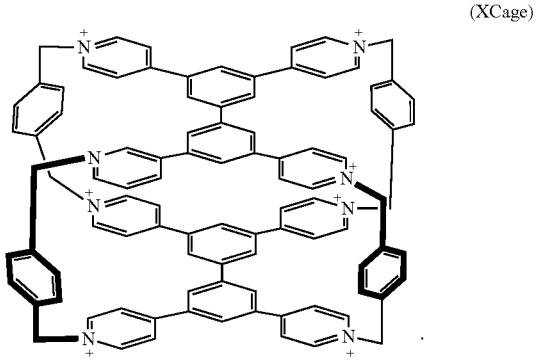

(XCage)

Another aspect of the invention includes receptor-substrate complexes. The complex may comprise a tricyclic octacationic cyclophane and a perylene diimide dye complexed therein. In some embodiments, the perylene diimide dye has a formula

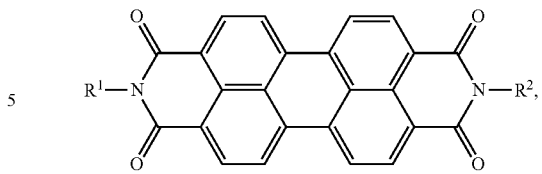

wherein $R^1$ and $R^2$ are independently selected from hydrogen, a substituted or unsubstituted, branched or unbranched, saturated or unsaturated $C_1$-$C_6$ alkyl, a substituted or unsubstituted aryl, or —$OCH_2CH_2(OCH_2CH_2)_n$—OR where R is hydrogen or a substituted or unsubstituted, branched or unbranched, saturated or unsaturated $C_1$-$C_6$ alkyl and n is an integer greater than or equal to 0.

Another aspect of the invention includes crystalline compositions comprising any of the complexes described herein.

Another aspect of the invention includes a method for fluorescence spectroscopy. The method may comprise providing any of the complexes described herein, irradiating the complex with an irradiation source, and detecting an emission signal from the complex.

Another aspect of the invention includes a method for live cell imaging. The method may comprise contacting a cell with any of the complexes described herein, irradiating the cell with an irradiation source, and detecting an emission signal from the complex.

Another aspect of the invention includes a method for preparing a receipt-substrate complex. The method may comprise providing a tricyclic octacationic cyclophane, providing a perylene diimide dye, and contacting the tricyclic octacationic cyclophane and the perylene diimide dye.

These and other aspects of the invention will be further described herein.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

(FIG. 1A) Synthesis of XCage.8CF$_3$CO$_2$. (FIG. 1B) Solid-state superstructures of Perylene ⊂ XCage$^{8+}$ obtained from single-crystal X-ray crystallography. Counterions and solvents are omitted for the sake of clarity FIG. 2. Substrates molecules evaluated in the present study. Perylene and caffeine are used as competitive substrates for displacement studies. PDI2 has been modified with polydispersed PEG chains to enhance its solubility in water FIGS. 3A-3E. (FIG. 3A) Plane and (FIG. 3B) side-on views of the solid-state superstructure of PDI1 ⊂ XCage$^{8+}$ obtained from single-crystal X-ray crystallography. (FIG. 3C) Surface-area overlap analysis of PDI1 ⊂ XCage$^{8+}$. Half of XCage$^{8+}$ is deleted for the sake of clarity. 1: roof or floor; 2: pillar units; 3: total area of the PDI core; 4: overlapping area. (FIG. 3D) [N$^+$ . . . O=C] ion-dipole interaction distances in PDI1 ⊂ XCage$^{8+}$. (FIG. 3E) Electrostatic potential map of the PDI core FIGS. 4A-4B.

FIG. 14. Concentration dependent uptake of PDI2⊂XCage$^{8+}$ in MCF-7 cells. Bright field merged live-cell confocal microscopy images of MCF-7 cells after incubation with different concentrations (10, 1, 0.1, and 0.01 μM) of PDI2⊂XCage$^{8+}$ for 6 h. Scale bar is 20 μm.

DETAILED DESCRIPTION OF THE INVENTION

Figure 1A:
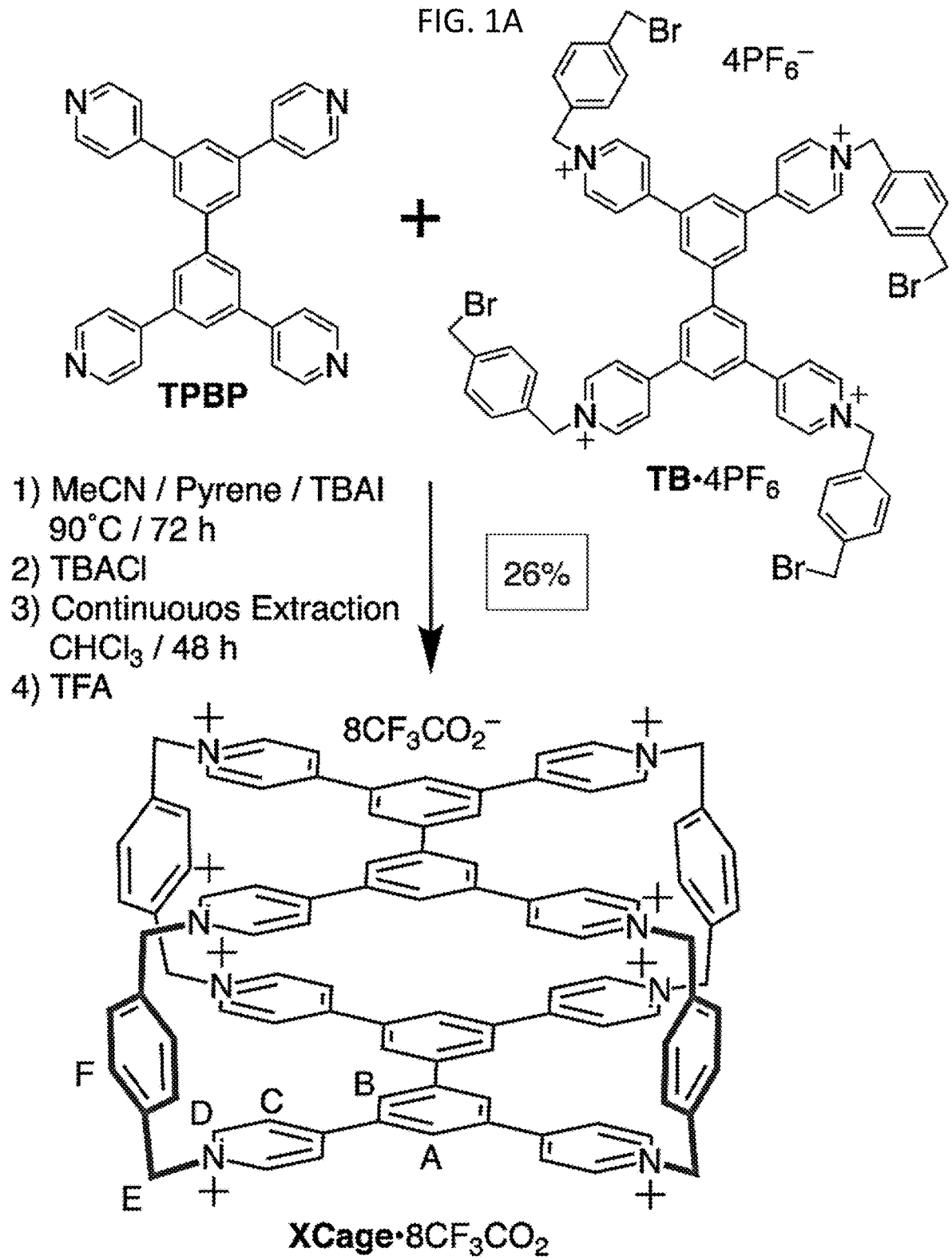
FIGS. 1A-1B.

Here, we report the synthesis of a tricyclic octacationic cyclophane, which exhibits complementary stereoelectronic binding towards perylene diimide dyes with picomolar affinity in water. The ultrahigh binding affinity is sustained by a large and rigid hydrophobic binding surface, which provides a highly favorable enthalpy and a slightly positive entropy of complexation. The receptor-substrate complex shows significant improvement in optical properties, including red-shifted absorption and emission, turn-on fluorescence, and efficient energy transfer. An unusual single-excitation, dual-emission, imaging study of living cells was performed by taking advantage of a large pseudo-Stokes shift, produced by the efficient energy transfer.

Herein, we report a new synthetic receptor that is tailored to provide a complementary stereoelectronic binding cavity for binding a dye, such as an aromatic dye like perylene diimide (PDI) dye, in water or other solvents. The receptor is a tricyclic octacationic cyclophane receptor featuring a roof-pillar-floor structure. Each of the roof and the floor are composed of a biphenyl unit having four pyridinium units extending therefrom. Pillars connect a pyridinium unit of the roof with another pyridinium unit of the floor. The biphenyl unit provides a large and flat binding surface, and four pillars connecting each of the four pyridinium units of the roof with another pyrinium unit of the floor results in a rigid cavity capable of hosting a dye substrate. The eight cationic pyridinium units provide both sufficient water solubility and complementary electronic binding sites for electron-rich moieties such as carbonyl groups. In some embodiments, the pillars comprise a xylylene unit.

In some embodiments, the cyclophane is

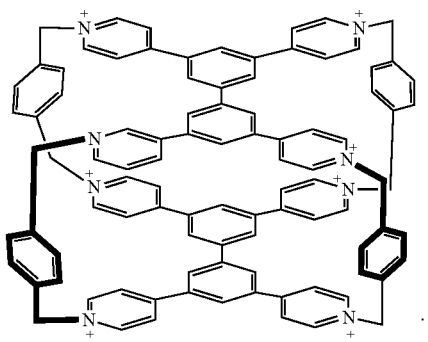

This cyclophane is referred to as XCage$^{8+}$ in view of its X-shaped structure. Four p-xylylene units serve as pillars with the ideal lengths (7.0 Å) to support aromatic [π . . . π] stacking interactions (2×3.5 Å) with an aromatic substrate, such as a PDI dye, in its cavity.

Receptor-substrate complexes may comprise a PDI dye. As used herein, a PDI dye has a perylene core

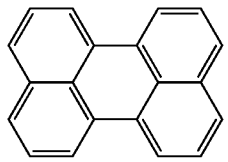

and two imide moieties covalently bound thereto to form a seven-membered ring system. In some embodiments, the PDI dye has a formula

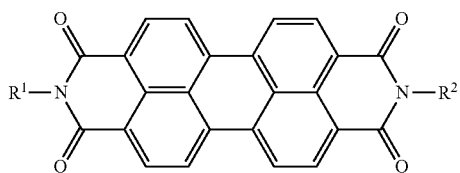

where each $R^1$ and $R^2$ are independently selected from hydrogen, a substituted or unsubstituted, branched or unbranched, saturated or unsaturated $C_1$-$C_6$ alkyl, a substituted or unsubstituted aryl, or —$OCH_2CH_2(OCH_2CH_2)_n$—OR where R is hydrogen or a substituted or unsubstituted, branched or unbranched, saturated or unsaturated $C_1$-$C_6$ alkyl and n is an integer greater than or equal to 0. In some embodiments, n is between 0 and 150. $R^1$ and $R^2$ may be optionally substituted with —NRR', —NRR'R", —SR, —C(=O)OR, —OR, —C≡R. Each of R, R', and R" may be independently selected from hydrogen, a substituted or unsubstituted, branched or unbranched, cyclic or acyclic, saturated or unsaturated $C_1$-$C_6$ alkyl, or a substituted or unsubstituted, branched or unbranched, cyclic or acyclic, saturated or unsaturated amine. Exemplary R, R', and R" include, without limitation, —H, —$CH_3$, —CH, —$CH_2CCH$,

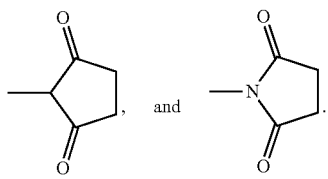

Exemplary PDI dyes include, but are not limited to,

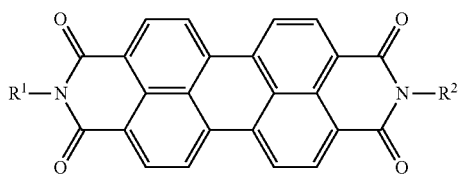

where $R^1$ and/or $R^2$ is selected from

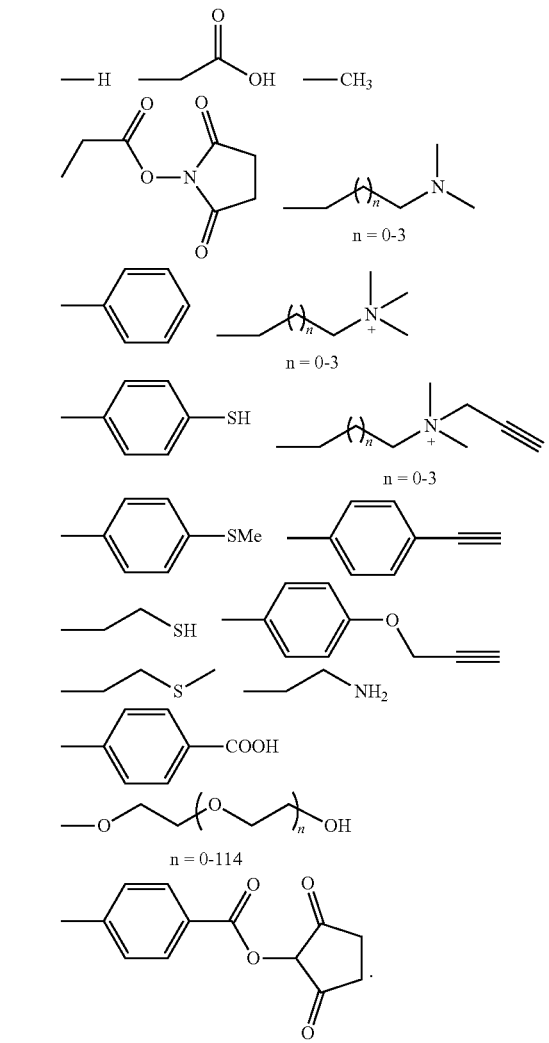

In some embodiments, the PDI dye includes R selected from —$CH_2CH_2NMe_2$ or —$CH_2CH_2[OCH_2CH_2]_{44}OMe$. When R comprises a polyethylene glycol (PEG) chain, the PEG chain may be polydisperse and the notation $[OCH_2CH_2]_n$ may indicate an average molecular weight as measured by electrospray ionization mass spectrometry or other suitable measurement technique.

The eight cationic pyridinium units of the cyclophane provide complementary electronic binding sites for the four divergent carbonyl groups in the PDI molecule. The resulting PDI⊂XCage·8CF$_3$CO$_2$ complex, which exhibits picomolar binding affinity in water, is enthalpically driven along with a small favorable entropic component. Moreover, the strong binding is accompanied by a significant improvement in optical properties, including turn-on fluorescence, red-shifted absorption and emission, in addition to efficient energy transfer, which remains effective under cell-imaging conditions. The energy transfer results in a large pseudo-Stokes shift that is utilized in achieving a dual color imaging study of living cells using a single light excitation.

PDI-based dyes have superior photophysical properties and wide range of applications in materials science[35] and biotechnology[36]. Encapsulations of PDI dyes have been explored[37,38] using cucurbit[8]uril and also a tetracationic cyclophane, known[28] as ExBox[4+]; significant improvements in photophysical properties of PDI dyes were observed in water. The affinity constants involving both these receptors remain around $10^5$ M$^{-1}$ or lower in water. A closer inspection of these receptor-substrate pairs reveals that neither synthetic receptor is able to encapsulate completely the PDI molecule since the relatively large size of PDI imposes a particular challenge in identifying suitable receptors.

Synthesis of XCage.8CF$_3$CO$_2$

Figure 8:
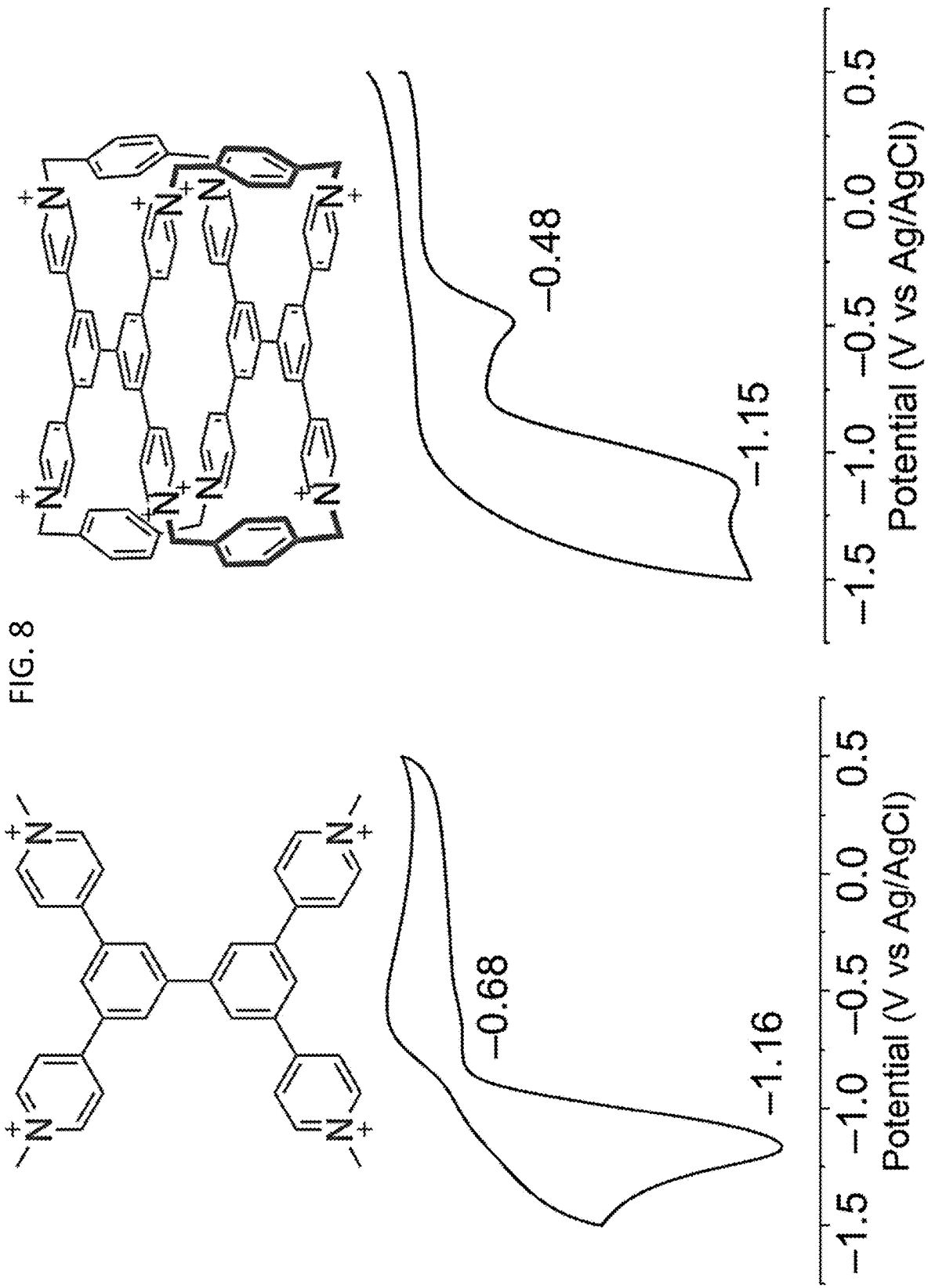
FIG. 8. First cycle of cyclic voltammetry data for TM$^{4+}$ (left) and XCage$^{8+}$ (right)

XCage.8CF$_3$CO$_2$ was prepared (FIG. 1A) in three steps from commercially available starting materials. The key building block TB.4PF$_6$ can be easily accessed by Suzuki coupling, followed by alkylation of pyridine units in 91% overall yield without the need of column chromatography. XCage.8CF$_3$CO$_2$ was obtained by a template-assisted synthesis with the help of TBAI as a catalyst.[39] Pyrene was used as a template and was subsequently removed by continuous liquid-liquid extraction. In the absence of template, no product could be isolated on account of the structural flexibility of TB.4PF6. In the absence of template, no product could be isolated on account of the structural flexibility of TB.4PF6. The presence of pyrene template helps preorganize and rigidify the precursor and facilitate XCage$^{8+}$ formation. Moreover, the template also helps visualize the formation of XCage$^{8+}$, which forms a yellow precipitate from the reaction mixture after its complexation with pyrene. The presence of pyrene template helps preorganize and rigidify the precursor and facilitate XCage$^{8+}$ formation. Moreover, the template also helps visualize the formation of XCage$^{8+}$, which forms a yellow precipitate from the reaction mixture after its complexation with pyrene. The crude product was isolated by precipitation with TBACl and further purified by reverse-phase column chromatography. After anion exchange using TFA, XCage$^{8+}$ was obtained as its CF$_3$CO$_2$$^-$ salt in 26% isolated yield. XCage.8CF$_3$CO$_2$ is highly soluble in water and MeOH, and slightly soluble in MeCN. It emits a blue fluorescence (10% quantum yield) in the range of 350-550 nm in water. The absolute fluorescent quantum yield of XCage.8CF$_3$CO$_2$ in water was measured using an integrating sphere detector. The absolute fluorescent quantum yield of XCage.8CF$_3$CO$_2$ in water was measured using an integrating sphere detector. The results of cyclic voltammetry experiments (FIG. 8) reveal a nonreversible redox process in Me$_2$SO. The nonreversible redox process of XCage.8CF$_3$CO$_2$ in Me$_2$SO is a result of the poor solubilities of the neutral species upon reduction. After the first redox cycle, precipitations were observed on electrodes, and no redox signal could be further detected. The nonreversible redox process of XCage.8CF$_3$CO$_2$ in Me$_2$SO is a result of the poor solubilities of the neutral species upon reduction. After the first redox cycle, precipitations were observed on electrodes, and no redox signal could be further detected.

X-Ray Crystallographic Analysis

Figure 1B:
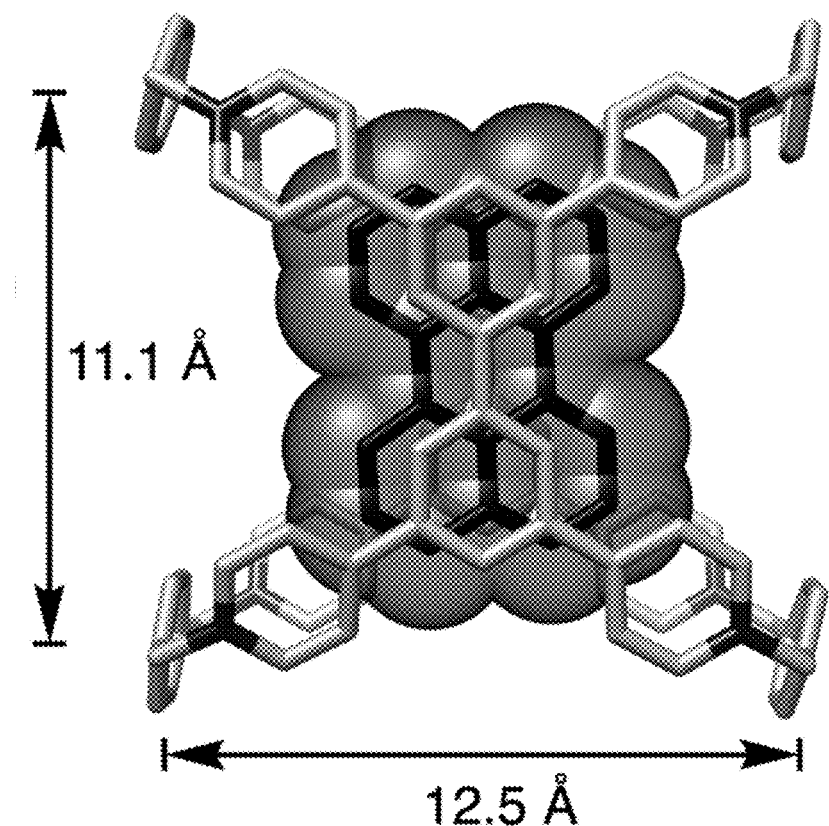
Figure 1B:
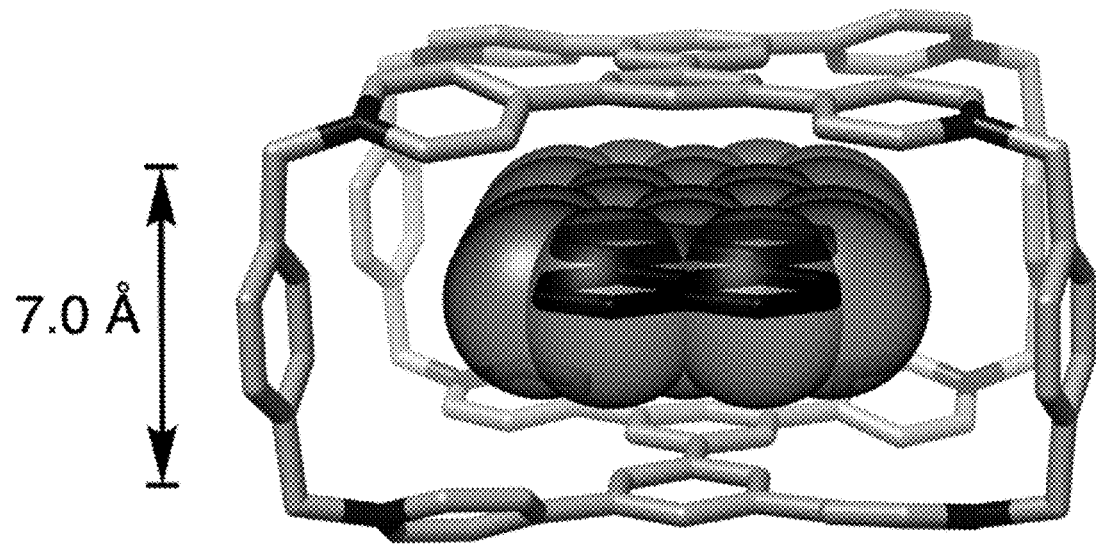
Figure 9:
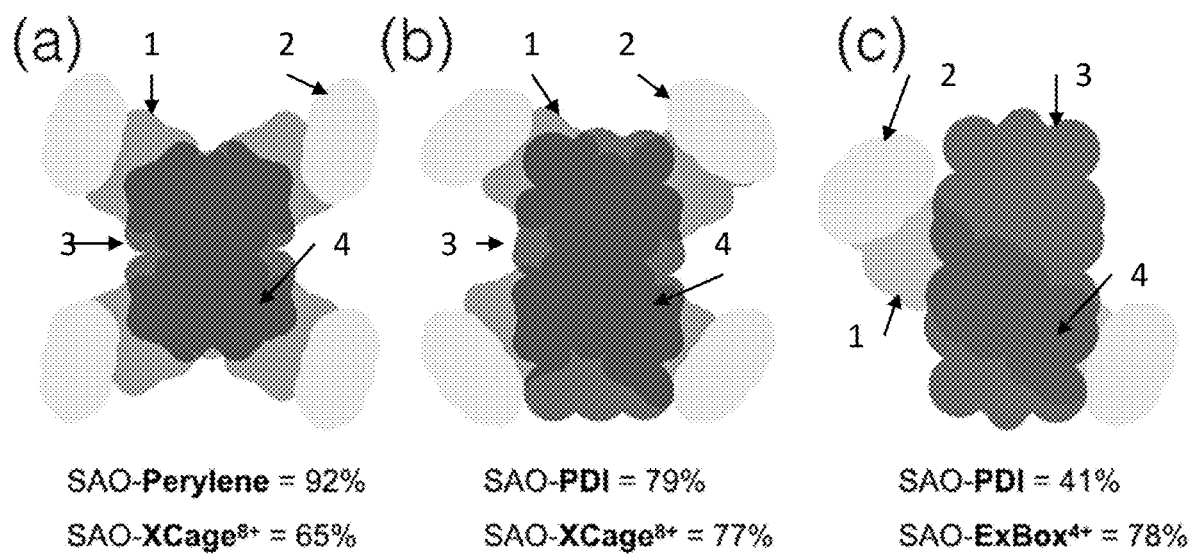
FIG. 9. Surface-area overlap (SAO) images for (a) Perylene⊂XCage$^{8+}$, (b) PDI⊂XCage$^{8+}$, and (c) PDI⊂ExBox$^{4+}$.
Figure 10:
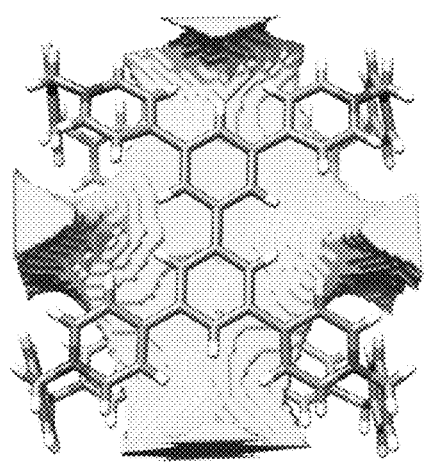
FIG. 10. The cavity volume (shown in yellow) of XCage$^{8+}$ based on pro-molecular density at 0.0001 a.u.
Figure 11:
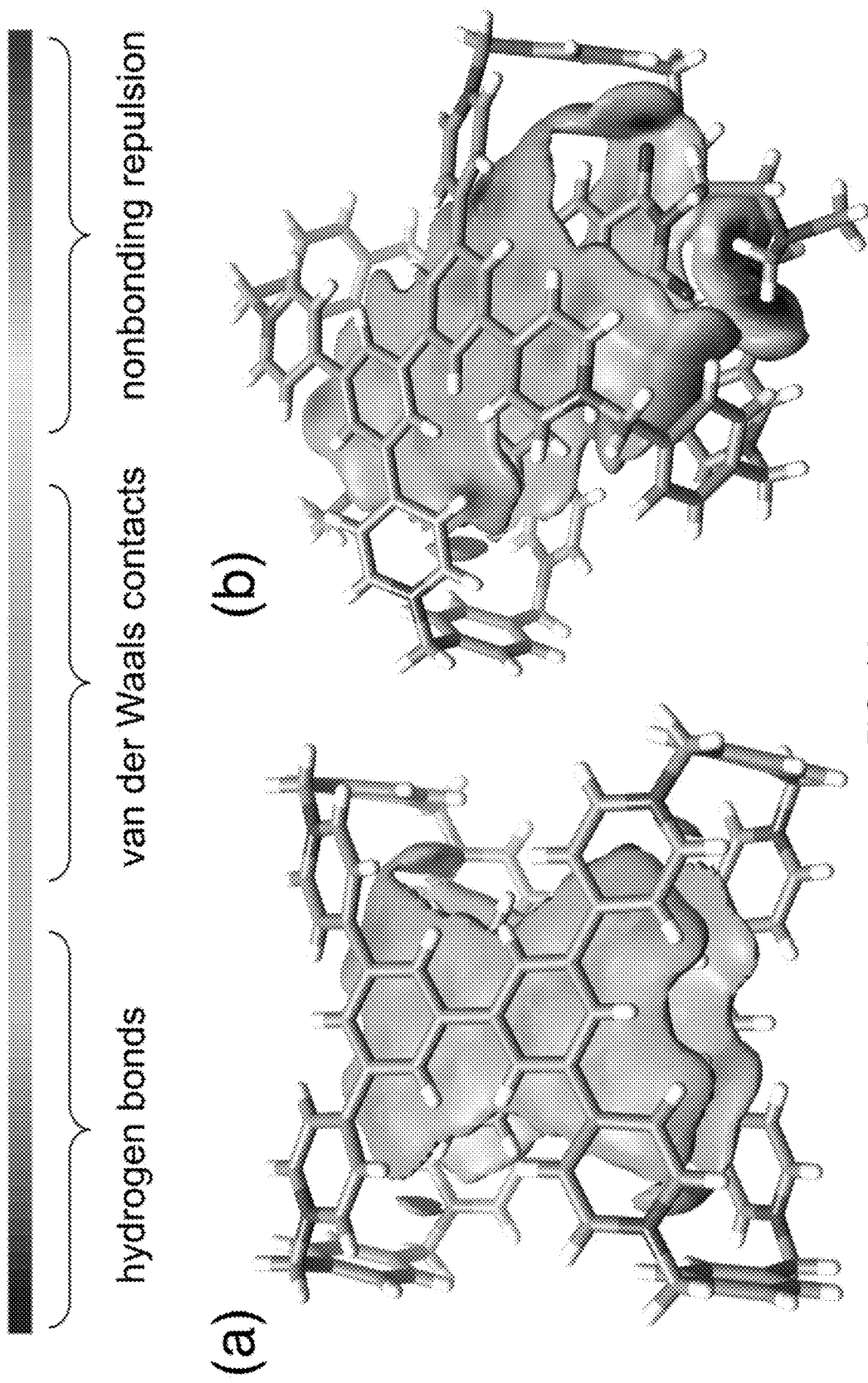
FIG. 11. (a) Intermolecular binding iso-surface of Perylene∈XCage$^{8+}$. (b) Intermolecular binding iso-surface of PDI1⊂XCage$^{8+}$. $\Delta\kappa^{inter}(\rho)$=0.002 a.u. Iso-surfaces are shaded according to a BGR scheme over the range −0.05<sign($\lambda_2$)$\rho$<+0.05 a.u. Scale bar: color codes for non-covalent bonding surfaces predicted by IGM analysis.

Numerous attempts to grow the single crystals of XCage$^{8+}$ with various counterions did not meet with success. Large (>100 μm in diameter) block-like crystals can be obtained by slow diffusion of Et$_2$O into a MeOH solution of XCage.8CF$_3$CO$_2$. These crystals showed poor X-ray diffraction, which prevented further structural determination. Fortunately, a single crystal of Perylene⊂XCage.8CF$_3$CO$_2$ was obtained by slow vapor diffusion of iPr$_2$O into a MeOH solution of Perylene⊂XCage.8CF$_3$CO$_2$. The solid-state structure of XCage.8CF$_3$CO$_2$ (FIG. 1B) reveals that it has a box-like cavity with dimensions of 12.5×11.1×7.0 Å. The cavity volume (FIG. 10) is estimated to be around 384 Å$^3$, which is comparable[44] with the cavity volume of cucurbit [8]uril. The roof and floor are parallel and supported by four p-xylylene pillars with an ideal distance (7.0 Å) for aromatic [π . . . π] stacking interactions. The large binding surface (FIG. 9) of XCage$^{8+}$ covers 92% of the van der Waals surface of Perylene, which is sandwiched symmetrically between the roof and the floor. Moreover, the p-xylylene pillars provide further [CH . . . π] interactions with Perylene as revealed[45,46] by an independent gradient model (IGM) analysis (FIG. 11).

Figure 2:
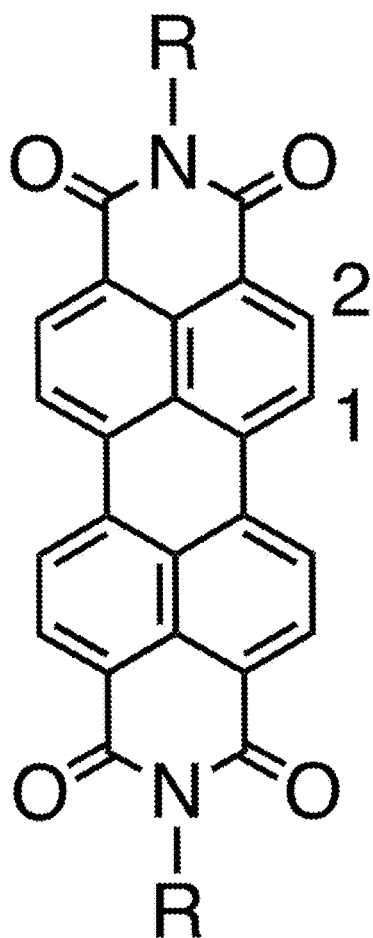
Figure 2:
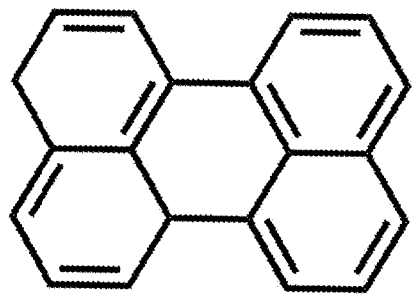
Figure 2:
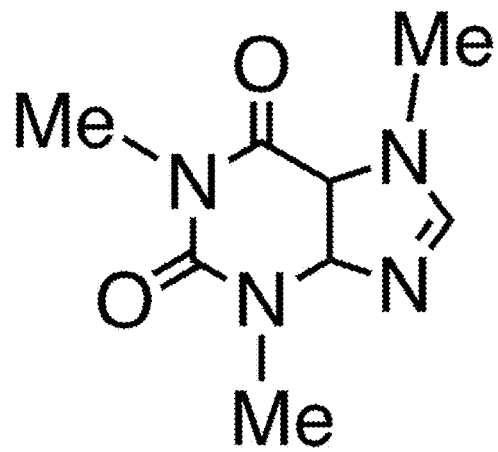

A model compound PDI1 (FIG. 2) was synthesized in order to obtain the single-crystal superstructure of its 1:1 complex with XCage$^{8+}$. Like other PDI dyes, PDI1 is poorly soluble in most solvents. In the presence of XCage.8CF$_3$CO$_2$, however, PDI1 can be dissolved readily in solvents such as H$_2$O, MeOH, MeCN, DMF and Me$_2$SO. A single crystal of PDI1⊂XCage.7PF$_6$·OH was obtained by slow diffusion of Et$_2$O into a solution of PDI1⊂XCage.8PF$_6$ in MeCN. The solid-state superstructure (FIG. 3D) reveals that each carbonyl group in PDI1 is sandwiched between two pyridinium units with an average [C=O . . . N$^+$] distance of 4.4 Å, which is the same [C=O . . . N$^+$] distance as that observed[47] in the diamantane⊂cucurbit[7]uril complex. There are in total eight [C=O . . . N$^+$] ion-dipole interactions within the complex, PDI1⊂XCage$^{8+}$. The core of PDI1 is sandwiched between the two biphenyl units as a result of aromatic [π . . . π] stacking interactions and separated by a distance about 3.7 Å from the roof and the floor. A surface-area overlay analysis shows that 80% of the van der Waals surface of the PDI1 core overlaps with XCage$^{8+}$. A similar analysis performed on a single crystal of a catenane shows[48] that only 40% of the PDI core overlaps with the ExBox$^{4+}$ component.[49] Thus, XCage$^{8+}$ provides twice the binding surface area compared to that of the ExBox$^{4+}$ component in the catenane. IGM analysis reveals that PDI is enveloped by favorable van der Waals interactions with the biphenyl-containing roof and floor, as well as from the pyridinium and p-xylylene units. Moreover, the carbonyl groups on PDI1 are involved in polar [C=O . . . HC] interactions with p-xylylene protons on XCage$^{8+}$. Interestingly, the planar surface of PDI1 was found to be slightly twisted (12°) in the bay region as a result of its aromatic [π . . . π] stacking interactions with the biphenyl-containing binding surfaces, which also exhibits a slightly twisted plane with a dihedral angle of 19°. Such induced-fit binding is a well-established phenomenon[51] in receptor-substrate binding pairs in biological systems.

NMR Spectroscopy and Mass Spectrometry in Solution

Figure 4A:
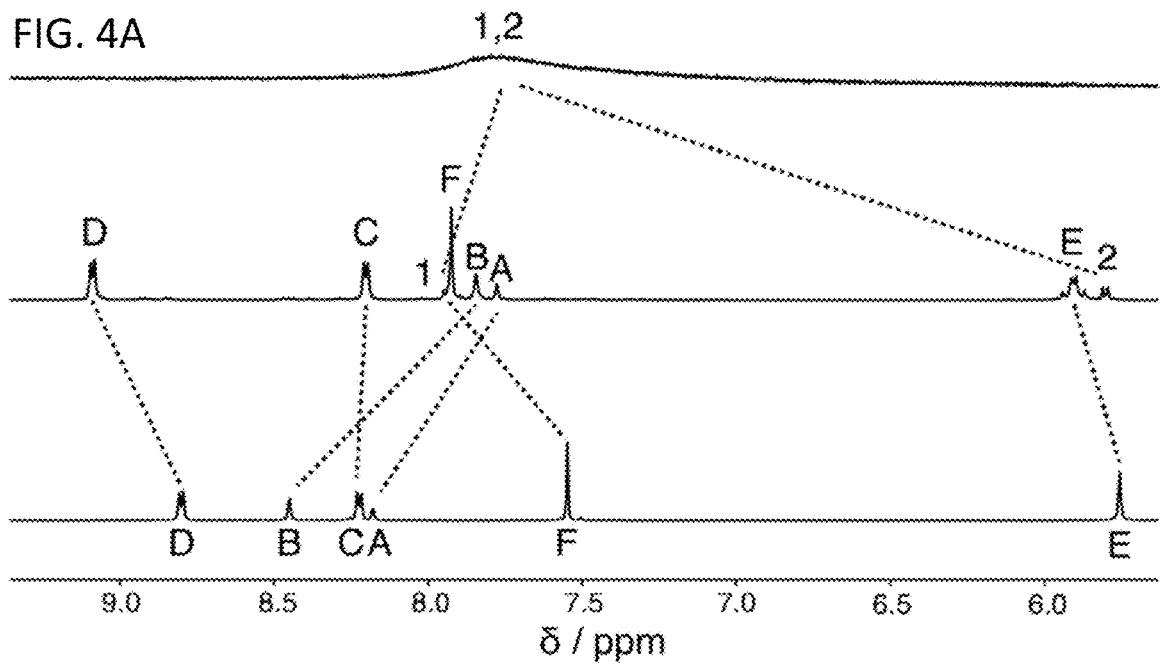
(FIG. 4A) $^1$H NMR (500 MHz, $D_2O$, 25° C.) spectra of PDI2 (top), PDI2⊂XCage.8CF$_3$CO$_2$ (middle), and XCage.8CF$_3$CO$_2$ (bottom).
Figure 4B:
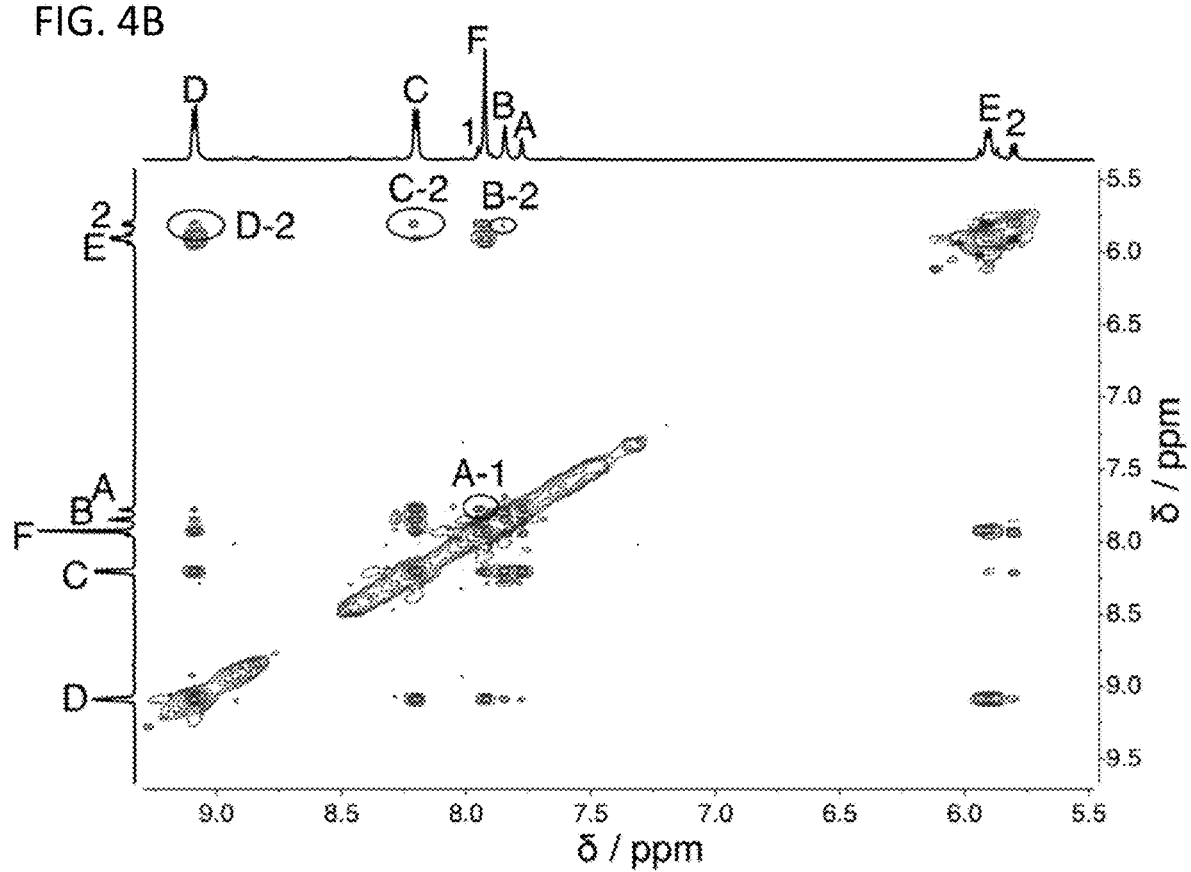
(FIG. 4B) $^1$H-$^1$H NOESY (500 MHz, $D_2O$, 25° C.) of PDI2⊂XCage.8CF$_3$CO$_2$. Protons labels are shown in FIG. 1 and FIG. 2. All samples were measured at 1.5 mM concentration FIGS. 5A-5D.
Figure 7:
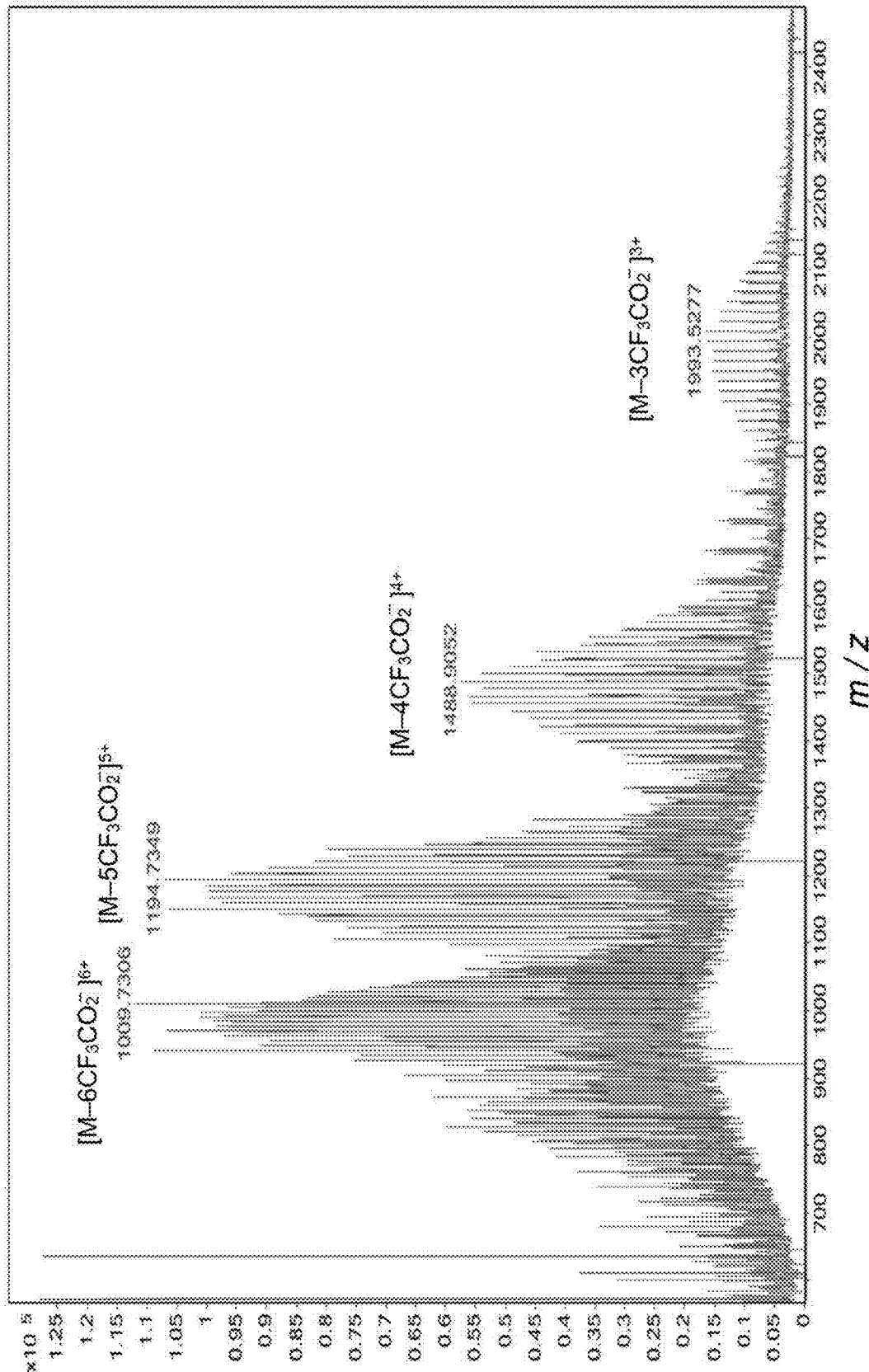
FIG. 7. HRMS-ESI Spectrum of PDI2⊂XCage.8CF$_3$CO$_2$

In order to investigate the molecular recognition between XCage.8CF$_3$CO$_2$ and PDI in water, a water-soluble PDI2 (FIG. 2) flanked with two mPEG$_{2000}$ chains was synthesized. PDI2 is polydispersed with an average molecular weight about 4000 according to electrospray ionization mass spectrometry. A 1:1 mixture of PDI2 and XCage.8CF$_3$CO$_2$ in D$_2$O produced PDI2⊂XCage.8CF$_3$CO$_2$ instantly in quantitative yield. Diagnostic changes in chemical shift, indicating complex formation, were revealed by comparison (FIG. 4A) of the $^1$H NMR spectra of PDI2, PDI2⊂XCage.8CF$_3$CO$_2$ and XCage.8CF$_3$O$_2$. Large upfield shifts of the signal for protons A (Δδ=−0.41 ppm) and protons B (Δδ=−0.61 ppm) on XCage.8CF$_3$CO$_2$, together with a significant upfield shift of the signal for protons 2 (Δδ=−1.98 ppm) on PDI2, indicate the presence of aromatic [π . . . π] stacking interactions between PDI2 and the biphenyl units. Meanwhile, large downfield shifts of the signal for protons D (Δδ=+0.29 ppm) and protons F (Δδ=+0.37 ppm) are a good indication of polar interactions between the imide carbonyl groups on PDI2 and XCage.8CF$_3$CO$_2$ protons from both the pyridinium and xylylene moieties. A NOESY spectrum (FIG. 4B) confirmed the threaded structure with through-space corrections between protons 2 on PDI2 and protons B, C and D on XCage.8CF$_3$CO$_2$. ESI-MS (FIG. 7) confirmed the formation of PDI2⊂XCage.8CF$_3$CO$_2$ in water by revealing several peaks clustered around m/z 2000, 1500, 1200 and 1000, corresponding to different charged states of PDI2⊂XCage.8CF$_3$CO$_2$ along with the loss of between three and six CF$_3$CO$_2^-$ counterions. The NOESY spectrum was obtained using 0.2 s mixing time. The $^1$H NMR spectrum of PEG chains were found to split into several peaks between 3.05 ppm and 4.20 ppm; these peaks also reveals through-space correlations with XCage$^{8+}$ in NOESY experiments. An analogous $^1$H NMR spectroscopic experiment, designed to follow the formation of PDI2⊂XCage.8CF$_3$CO$_2$ in MeCN, is described in the Supporting Information.

Photophysical Properties

Figure 5A:
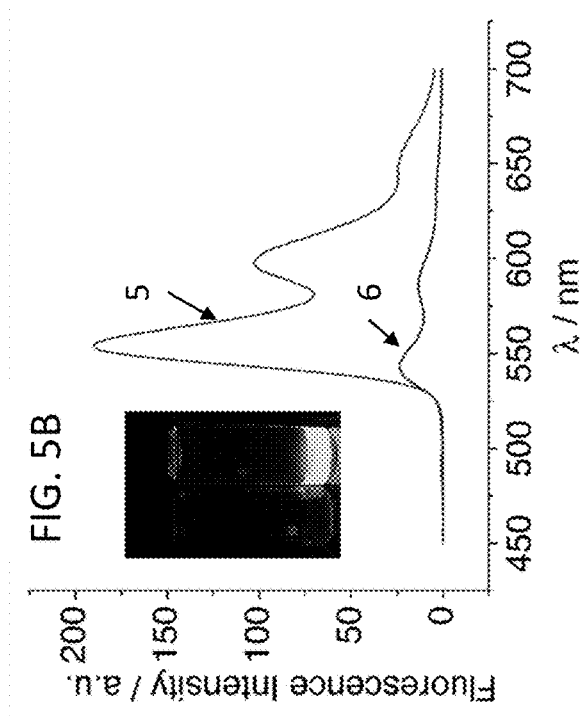
(FIG. 5A) Absorption and (FIG. 5B) emission (ex: 440 nm) spectra of PDI2 (6) and PDI2⊂XCage.8CF$_3$CO$_2$ (5) in water: inserts show aqueous solutions of PDI2 (left) and PDI2⊂XCage.8CF$_3$CO$_2$ (right) under day light and UV light (ex: 365 nm).
Figure 5B:
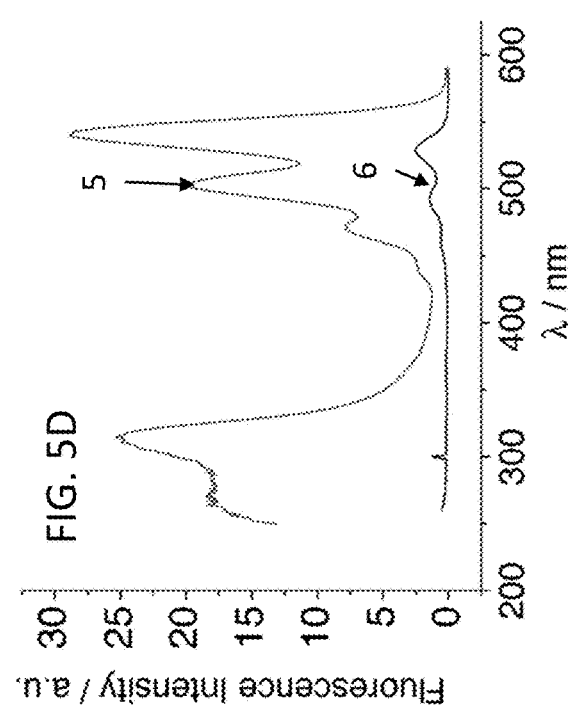
(FIG. 5C) Emission spectra (ex: 290 nm) of PDI2 (6) and PDI2⊂XCage.8CF$_3$CO$_2$ (5) in water.
(FIG. 5D) Excitation spectra (em: 600 nm) of PDI2 (6) and PDI2⊂XCage.8CF$_3$CO$_2$ (5) in water FIGS. 6A-6D.
Figure 5C:
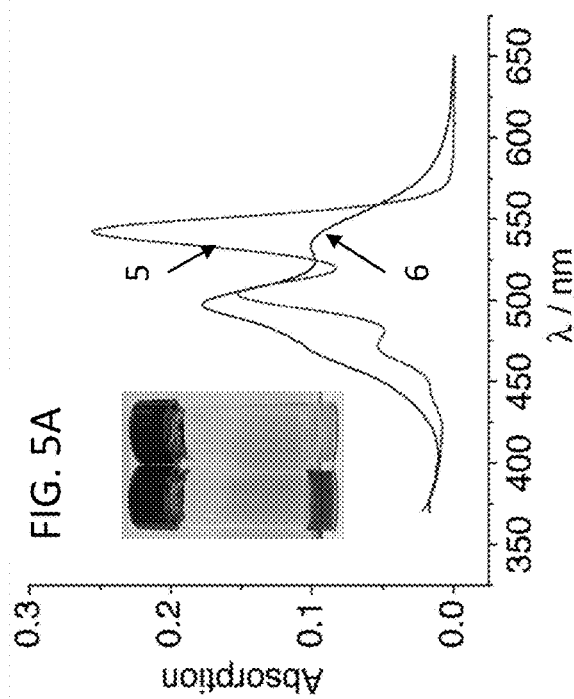

Encapsulation of PDI2 by XCage.8CF$_3$CO$_2$ induces several distinctive changes in photophysical properties. In the UV-Vis spectra in MeCN, PDI2 shows three sharp absorption peaks at 456, 484, and 520 nm, corresponding to the non-aggregated state of PDI2. This compound emits a bright yellow fluorescence with a 66% fluorescence quantum yield. In the presence of XCage.8CF$_3$CO$_2$, both the absorption and emission maxima of PDI2 are red shifted (23-25 nm), whereas the fluorescence quantum yield remains unchanged. On the other hand, PDI2 is highly aggregated in water, as indicated (FIG. 5A) by the broad absorption peaks[53] and a low fluorescence quantum yield (4%). The observed weak fluorescence of PDI2 originates from residual monomeric species, judging from its excitation spectrum. Upon the addition of one molar equivalent of XCage.8CF$_3$CO$_2$, the color of the PDI2 solution changes instantly from dark red to bright orange; three distinctive absorption peaks at 472, 504, and 542 nm, the characteristic signature of monomeric PDI in solution, were observed. Meanwhile, the fluorescence quantum yield of PDI2⊂XCage.8CF$_3$CO$_2$ in water increases up to 63%, which is close to the brightness of the complex in MeCN. Furthermore, the excitation and emission maxima of PDI2⊂XCage.8CF$_3$CO$_2$ are red shifted (9-15 nm), and its fluorescence lifetime increases from 4.7 to 7.3 ns when compared with PDI2. Notably, the fluorescence of PDI2⊂XCage.8CF$_3$CO$_2$ remains bright, even at high concentrations (>1 mM) in water, i.e., the condensed charges on PDI2⊂XCage.8CF$_3$CO$_2$ prevent it from aggregating.

Figure 5D:
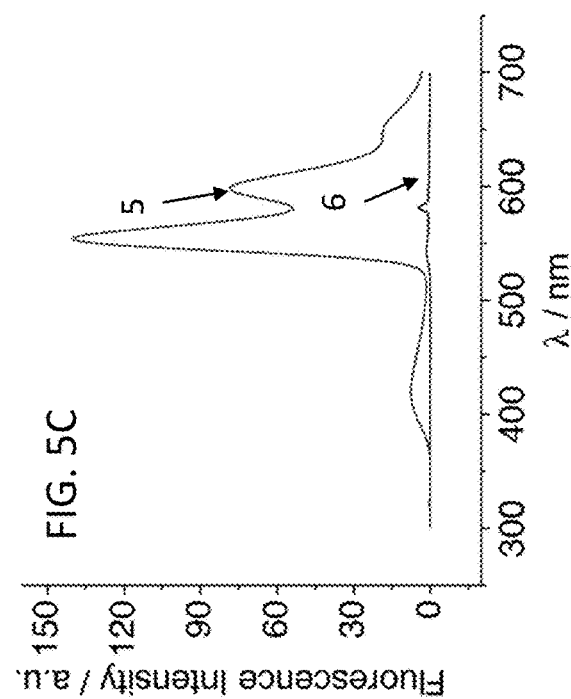

There is an efficient energy transfer from XCage.8CF$_3$CO$_2$ to PDI2 in both MeCN and H$_2$O. In the excitation spectrum of PDI2⊂XCage.8CF$_3$CO$_2$, we observed a strong excitation peak around 300 nm, where XCage.8CF$_3$CO$_2$ absorbs light. Remarkably, in MeCN, the fluorescence intensity of PDI2⊂XCage.8CF$_3$CO$_2$, as a result of energy transfer, is 150% higher than that of the complex under direct excitation at 542 nm, suggesting a superior antenna effect. In water, the energy transfer process (FIG. 5D) produces 86% of its original fluorescence intensity. By comparing the fluorescent emission of XCage.8CF$_3$CO$_2$ and PDI2⊂XCage.8CF$_3$CO$_2$ at 350-525 nm, the energy transfer efficiencies are determined to be quantitative in MeCN and 90% in water.

Binding Kinetics and Thermodynamics

The changes in optical properties induced on PDI2⊂XCage.8CF$_3$CO$_2$ complex formation enable a facile tracking of the recognition process. The kinetics of threading PDI2 into XCage.8CF$_3$CO$_2$ in water was tracked by turn-on fluorescence as a function of time. The kinetic profile was fitted to a second order kinetic model and revealed $k_{on}$= (4.8±1.1)×10$^5$ M$^{-1}$s$^{-1}$. The half-life at 0.1 μM was calculated to be 21 s. Such rapid complex formation of PDI2⊂XCage.8CF$_3$CO$_2$ in water is remarkable when one considers the threading process that involves the chain end of mPEG$_{2000}$ polymer finding a "correct" cavity entrance and then exiting at the right opening of the tricyclic cage. This observation agrees with the reported literature[55-57] that threading a PEG polymer through a macrocycle is rapid in water.

The binding constants (Table 1) were determined by fluorescence titration and isothermal titration calorimetry (ITC). Displacement titration experiments monitored by fluorescence were performed in order to determine the high binding affinity between PDI2 and XCage.8CF$_3$CO$_2$. An effort to determine the binding constants between XCage$^{8+}$ and PDI2 using the displacement ITC method in both MeCN and water did not meet with success on account of the mutal aggregation among XCage$^{8+}$, competitors, PDI2, and their corresponding complexes. In MeCN, binding of XCage.8CF$_3$CO$_2$ was tested first of all using Perylene as a substrate. Its binding constant was found to be in the order of 10$^6$ M$^{-1}$, which is similar in magnitude to that of ExCage$^{6+}$.6PF$_6$ and about 86 times higher than that of ExBox$^{4+}$.4PF$_6$.[28,29] Next, we performed a competitive experiment, starting with a solution of XCage.8CF$_3$CO$_2$ and 50 molar equivalents of Perylene. PDI2 was titrated into the MeCN solution to displace Perylene from the cavity. The displacement titration was monitored by turn-on fluorescence and yielded a binding constant in the vicinity of 10$^9$ M$^{-1}$. The binding affinity between XCage.8CF$_3$CO$_2$ and PDI2 in MeCN is too high to be evaluated by ITC, and only the binding enthalpy could be extracted from the isotherm. The Gibbs free energy was estimated from fluorescent titrations which also provide a TΔS value. The formation of PDI2⊂XCage.8CF$_3$CO$_2$ in MeCN is mainly driven by favorable enthalpy with a small contribution from positive entropy. Compared with the binding of Perylene towards XCage.8CF$_3$CO$_2$, PDI2 shows a similar positive ΔS and also enjoys a more negative ΔH, which originates from the additional [C=O . . . N$^+$] ion-dipole interactions.

In order to evaluate the affinity between XCage.8CF$_3$CO$_2$ and PDI2 in water, we selected Caffeine as a competitor, considering its good solubility and structural similarity to PDI. The binding constants determined from both the fluorescence titration and ITC yielded similar results that are in the order of 10$^5$ M$^{-1}$. The binding constant between PDI2 and XCage.8CF$_3$CO$_2$ in water was subsequently measured in the presence of 1000 molar equivalents of Caffeine. As evaluated by the fluorescence titration, the binding constant between PDI2 and XCage.8CF$_3$CO$_2$ was determined to be 7.7×10$^{10}$ M$^{-1}$, i.e., $K_d$=13 pM. The formation of PDI2⊂XCage.8CF$_3$CO$_2$ in water is enthalpically driven with a small favorable entropic component. The binding enthalpy observed in water is 4 kcal mol$^{-1}$ higher when compared with that in MeCN, suggesting that the release of high energy water molecules provides[59] an extra contribution to the stability of PDI2⊂XCage.8CF$_3$CO$_2$ in addition to the large area [π-π] stacking and ion-dipole interactions. The small favorable entropy benefits[60] from the release of water into the bulk and the structural rigidity of both XCage.8CF$_3$CO$_2$ and PDI2.

Figure 12:
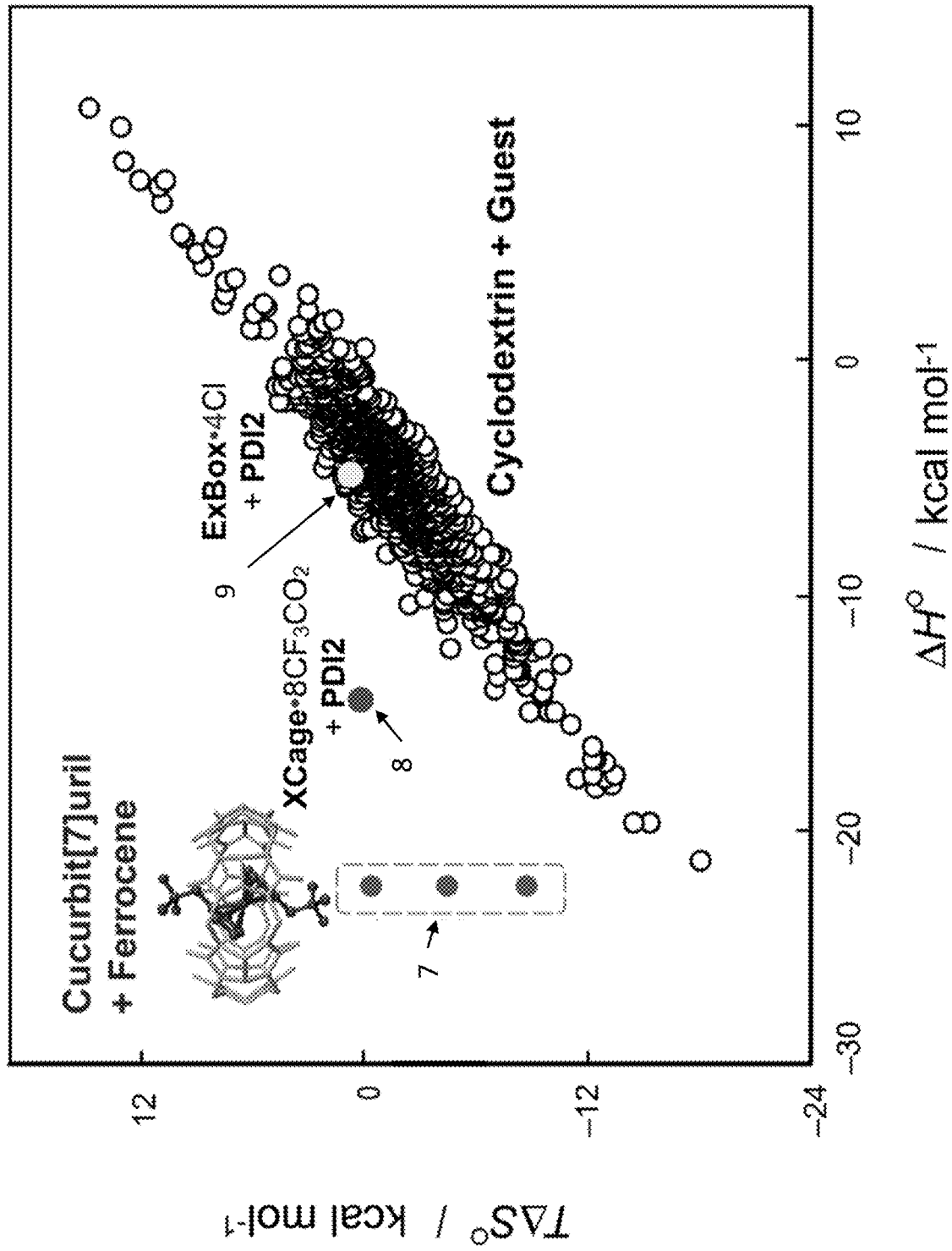
FIG. 12. The thermodynamic data obtained$^{S16}$ for binding of ferrocene derivatives with CB[7] (7), binding of PDI2 with XCage.8CF$_3$CO$_2$ (8) and ExBox.4Cl (9), and the enthalpy-entropy compensation plot for cyclodextrin-guest binding FIG. 13. MCF-7 cell viability after treatment with different concentrations of PDI2, XCage$^{8+}$, and PDI2⊂XCage$^{8+}$ for 24 h. Cell viability was measured using MTT assay. Error bars represent SD, N=4.

In order to illustrate the effect of the extended receptor surface on the affinity enhancement, we investigated the binding thermodynamics of ExBox.4Cl towards PDI2 in water. ExBox.4Cl shows a binding affinity of 2.0×10$^6$ M$^{-1}$ and a binding enthalpy of −7.4 kcal mol$^{-1}$. Compared with ExBox.4Cl, XCage.8CF$_3$CO$_2$ enhances the binding affinity by a factor of 38,000 and provides twice amount of binding enthalpy. This observation is in line with the results of surface area overlap analysis, which reveals that XCage[8+] provides twice the binding surface area towards the PDI binding core compared to that of ExBox[4+]. The extended binding surface results in significant gains in binding enthalpy ($\Delta\Delta H=-6.7$ kcal mol$^{-1}$), while the loss of binding entropy ($T\Delta\Delta S=-0.5$ kcal mol$^{-1}$) is trivial, leading to an obvious deviation[23] from the enthalpy-entropy compensation plots for cyclodextrin-guest complexation (FIG. 12) and significantly enhanced affinity. These results prove that cationic cyclophanes with large and rigid binding surface are promising candidates to achieve high binding affinities in water.

Fluorescence Imaging Studies

Figure 6A:
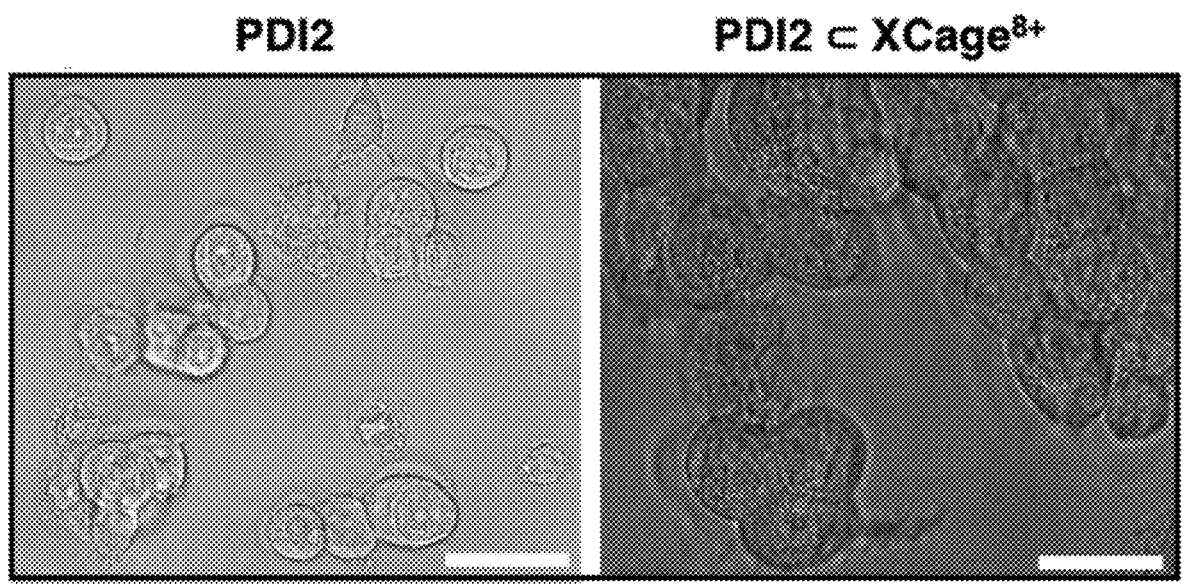
(FIG. 6A) Brightfield-merged micrograph of MCF-7 cells treated with PDI2 and PDI2⊂XCage$^{8+}$. Images were obtained using a 514 nm confocal laser with an emission window in the range of 530-580 nm. Scale bar: 20 μm.
Figure 6B:
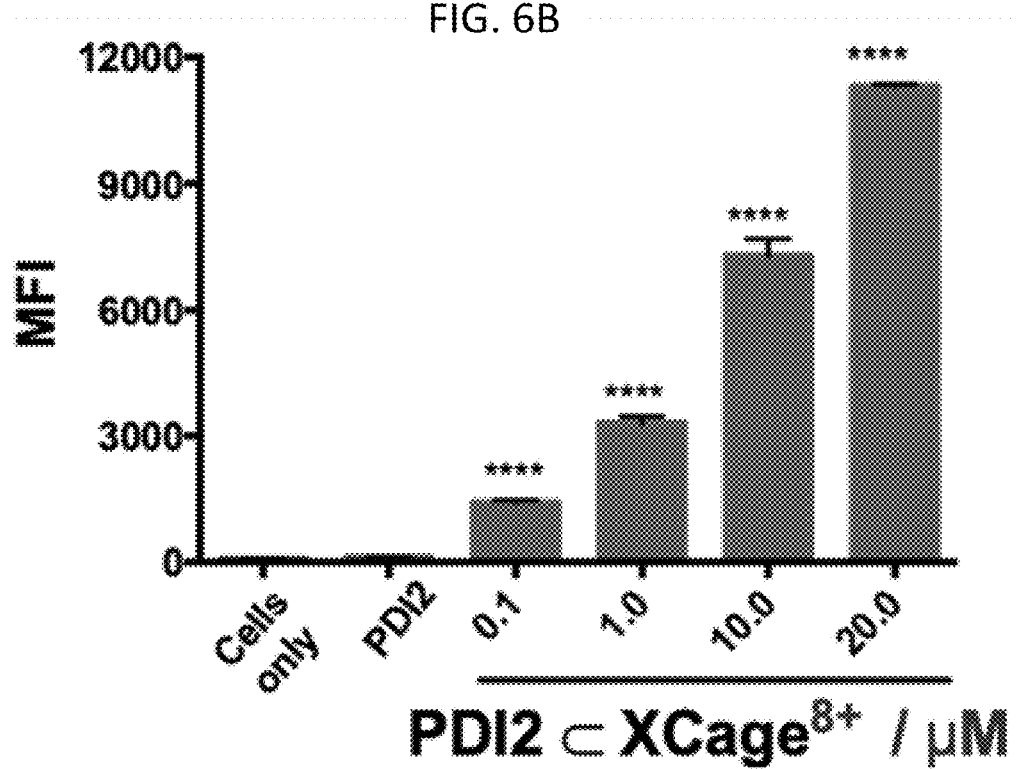
(FIG. 6B) Concentration dependent uptake of PDI2⊂XCage$^{8+}$ by MCF-7 cells analyzed by flow cytometry (ex: 552 nm) in the PE-Cy5 channel (em: 656-684 nm); MFI represents mean fluorescence intensity.
Figure 15:
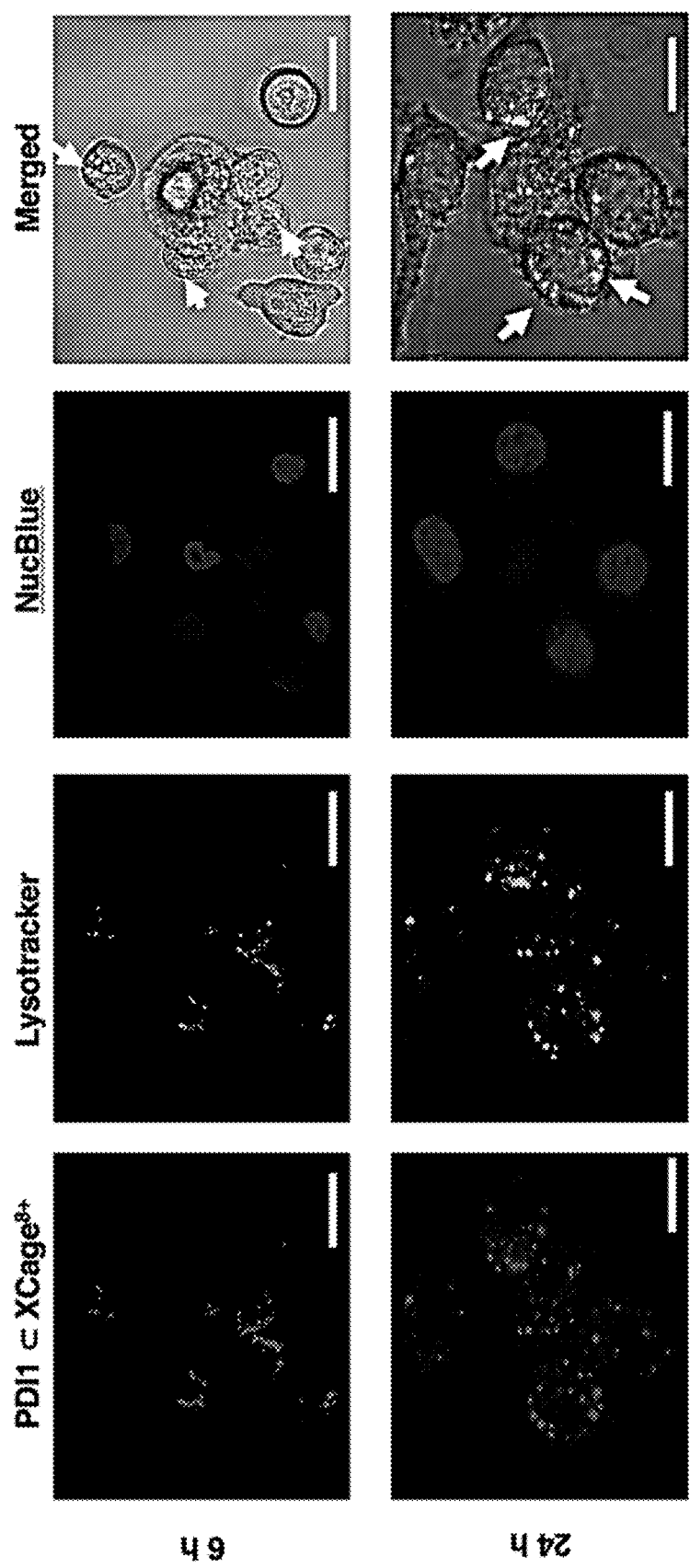
FIG. 15. Cellular co-localization of PDI2⊂XCage$^{8+}$ in MCF-7 cells. Live-cell confocal microscopy images of MCF-7 cells stained with Lysotracker green (lysosome stain) and NucBlue (nucleus stain) displaying endolysosomal co-localization of PDI2⊂XCage$^{8+}$ after incubation for 6 h (top row) and 24 h (bottom row) with MCF-7 cells. White arrows in the merged images show the co-localization of Lysotracker and PDI2⊂XCage$^{8+}$. Scale bar is 20 μm.

The potential application of these emergent properties was illustrated by fluorescence imaging and flow cytometry studies with MCF-7 cells, i.e., a human breast adenocarcinoma cell line. PDI2 ⊂ XCage.8CF$_3$CO$_2$ is non-toxic to MCF-7 cells and shows >95% cell viability at all concentrations tested (2.5-50 μM) (FIG. 13). Live-cell confocal microscopic images of MCF-7 cells were collected after incubation with 10 μM PDI2 or PDI2 ⊂ XCage.8CF$_3$CO$_2$ for 6 h. Brightfield-merged images show (FIG. 6A) no fluorescence after treatment with PDI2 and a strong fluorescence signal after PDI2 ⊂ XCage.8CF$_3$CO$_2$ treatment. The punctate signal of PDI2 ⊂ XCage.8CF$_3$CO$_2$ co-localizes with the lysotracker signal (FIG. 15), indicating the lysosomal localization of PDI2 ⊂ XCage.8CF$_3$CO$_2$ inside the cells. The concentration-dependent uptake, observed by confocal microscopic analysis and flow cytometry studies, shows (FIG. 6B and FIG. 14) that the PDI2 ⊂ XCage.8CF$_3$CO$_2$ could be detected inside MCF-7 cells at incubation concentrations as low as 0.1 μM. These results confirmed the superior fluorescence properties and high stability of PDI2 ⊂ XCage.8CF$_3$CO$_2$ complex, even at low concentrations under cell-imaging conditions.

Figure 6C:
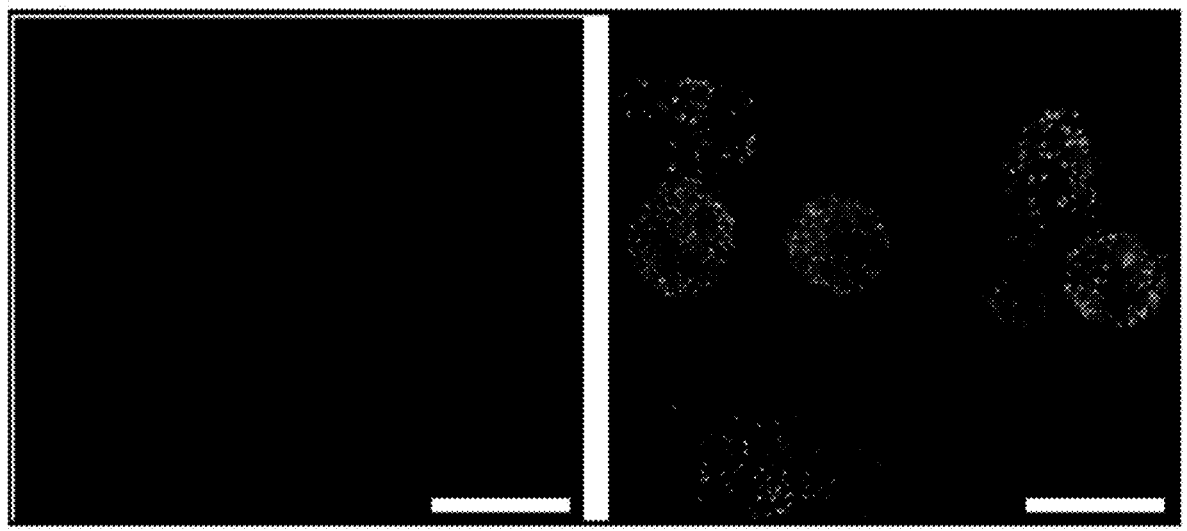
(FIG. 6C) Fluorescence micrograph of MCF-7 cells with PDI2 and PDI2⊂XCage$^{8+}$. Images were obtained using a DAPI excitation filter (ex: 381-399 nm) and a TRITC emission filter (em: 571-617 nm).
Figure 6D:
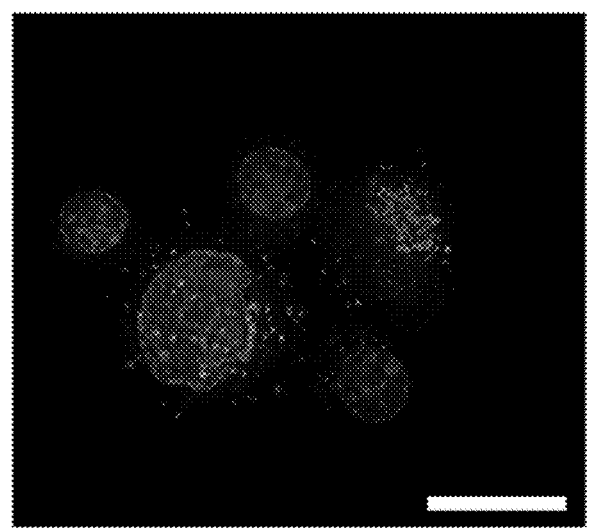
(FIG. 6D) Dual-color micrograph of MCF-7 cells with Hoechst and PDI2⊂XCage$^{8+}$. Images were obtained using a single DAPI excitation filter (ex: 381-399 nm) and two emission filters: DAPI emission filter (em: 411-459 nm) and TRITC emission filter (em: 571-617 nm). Scale bar: 25 μm.

PDI2 ⊂ XCage.8CF$_3$CO$_2$ produces (FIG. 5D) a similar fluorescence intensity as a result of efficient energy transfer when compared with the fluorescence by a direct excitation at 540 nm. Meanwhile, such an energy transfer process endows[61] the complex with a large pseudo-Stokes shift (239 nm). The bright fluorescence and large pseudo-Stokes shift are highly desirable for dual color imaging investigations[62] where a single light excitation can be used to excite two fluorophores that emit simultaneously in different wavelength regions. For this purpose, we tested the effectiveness of cell imaging using energy transfer. MCF-7 cells were incubated with 20 μM PDI2 ⊂ XCage.8CF$_3$CO$_2$ for 6 h and the live-cell fluorescence imaging was performed by widefield microscopy. When PDI2 ⊂ XCage.8CF$_3$CO$_2$ treated cells were excited using a DAPI excitation filter (ex: 381-399 nm), a bright fluorescence signal was detected (FIG. 6C) with a TRITC emission filter (em: 571-617 nm). As a control, 20 μM PDI2 treated cells did not show any fluorescence signal. Next, we tested the dual-color imaging, following incubation of MCF-7 cells with PDI2 ⊂ XCage.8CF$_3$CO$_2$ and Hoechst 33342 stain (Hoechst), a widely used nucleus stain with excitation and emission peaks at 350 and 461 nm, respectively. The micrograph (FIG. 6D) was obtained with a single DAPI excitation filter (ex: 381-399 nm) and two emission filters: DAPI (em: 411-459 nm) for Hoechst, and TRITC (em: 571-617 nm) for PDI2 ⊂ XCage.8CF$_3$CO$_2$. The Hoechst stain was localized in the nucleus and visualized as a blue color. Meanwhile, PDI2 ⊂ XCage.8CF$_3$CO$_2$ was visualized as the red punctate signals. These results demonstrate that the large pseudo-Stokes shift produced by efficient energy transfer can be utilized to achieve two-color channels imaging by a single light excitation, a procedure which has been explored previously with mutated fluorescent proteins[62] and synthetic dyes[63] that have large Stokes shifts. This property is highly desirable for the simultaneous study of two biological processes with advanced microscopic techniques, such as dual-color, single-laser fluorescence, cross-correlation spectroscopy[64] and multicolor stimulated emission depletion microscopy[65,66].

Conclusions

An octacationic tricyclic cyclophane XCage.8CF$_3$CO$_2$ has been designed and synthesized. XCage[8+] shows high complementary stereoelectronic binding towards PDI in water with picomolar affinity. The ultrahigh affinity of the complex is sustained by a blend of the hydrophobic effect as well as aromatic [π . . . π] stacking and ion-dipole interactions. This investigation proves that cationic cyclophanes with large and rigid surfaces are promising receptors for achieving high binding affinities in water. Meanwhile, the strong-affinity binding pair reported here offers an orthogonality to existed high-affinity binding pairs that can be used in noncovalent click chemistry.[13]

The encapsulated PDI dye results in improved optical properties, increased solubility and efficient energy transfer. The potential application of these emergent properties was demonstrated by a single-excitation dual-emission imaging of living cells with PDI2 ⊂ XCage.8CF$_3$CO$_2$ and Hoechst stain. While this research illustrates the bioimaging application of PDI2 ⊂ XCage.8CF$_3$CO$_2$, it is worth emphasizing that there is a multitude of applications of PDI in various other scientific fields as well. The high affinity and exceptional optical properties of PDI2 ⊂ XCage.8CF$_3$CO$_2$ provides for the manipulation of PDI dyes with an eye to a wide range of applications in the fields of single-molecule electronics,[67-69] photonic device,[70] materials science,[35] and molecular biology.[36]

Miscellaneous

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

General Information

Commercially available solvents and chemicals were purchased from Sigma-Aldrich and Fisher Scientific and used without further purification unless otherwise stated. Water was deionized, and micro filtered using Milli-Q water filtration station. Compounds PDI1[S1] and ExBox.4Cl[S2] were prepared using previously reported procedures. Thin layer chromatography (TLC) was performed on silica gel 60 F254 (E. Merck). Flash column chromatography was performed by Combiflash Rf 200 purification system. Reverse phase column chromatography was performed on Combiflash NEXTGEN 300+ system with SNAP ULTRA C18 cartridges which were purchased from Biotage. UV/Vis Absorption spectra were recorded in a glass cuvette using a UV-3600 Shimadzu spectrophotometer. Steady-state emission spectra were acquired in a quartz cuvette with an optical path-length of 10 mm containing the solution of interest using HORIBA Fluoromax4 spectrofluorometer, which was equipped with an integrating sphere for absolute photoluminescence quantum yield determination and time-correlated single-photon counting (TCSPC) module for emission decays. Nuclear magnetic resonance (NMR) spectra were recorded on Bruker AVANCE III 500 MHz spectrometer equipped with DCH CryoProbe, with working frequencies of 500 MHz for $^1$H and 125 MHz for $^{13}$C nuclei. Chemical shifts were reported in ppm relative to the signals corresponding to the residual non-deuterated solvents (CDCl$_3$: δ=7.26 ppm, CD$_3$CN: δ=1.94 ppm, CD$_3$OH: δ=4.74 ppm, D$_2$O: δ=4.74 ppm). High-resolution mass spectra were measured on an Agilent 6210 Time of Flight (TOF) LC-MS, using an ESI source, coupled with Agilent 1100 HPLC stack, using direct infusion (0.6 mL/min). Single crystal data were obtained on a Bruker Kappa APEX2 CCD diffractometer using Cu-Kα radiation. Detailed experimental procedures are provided below in the appropriate sections.

Synthetic Protocols

Scheme 1. Synthesis of TPBP

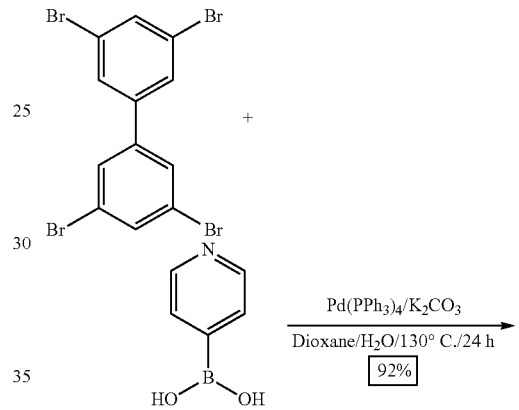

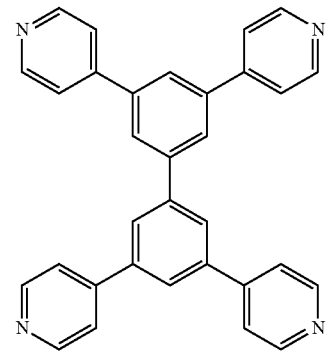

TPBP

TPBP: Dioxane was added to a solution of $K_2CO_3$ (5.2 g, 37.7 mmol) in $H_2O$ (15 mL). The resulting solution was degassed by bubbling $N_2$ gas for 10 min. 3,3',5,5'-Tetrabromo-1,1'-biphenyl (1.2 g, 2.6 mmol), 4-pyridinylboronic acid (2.0 g, 16.3 mmol), and $Pd(PPh_3)_4$ (160 mg, 0.13 mmol) were added to the degassed solution. The reaction mixture was degassed further using vacuum, followed by a $N_2$ flow cycle repeated three times before it was heated at 130° C. under reflux for 24 h. After cooling to room temperature, $H_2O$ (100 mL) was added to the reaction mixture, and the resulting solution was extracted by $CHCl_3$ (3×150 mL). The organic layers were combined and washed with $H_2O$ until no black suspension was observed in aqueous layer. After drying ($Na_2SO_4$), the organic solvents were removed under vacuum. The resulting yellow solid was washed with MeOH to obtain the product TPBP as an off-white solid (1.1 g, 92% yield). $^1$H NMR (500 MHz, $CDCl_3$) δ 8.73 (d, J=5.0 Hz, 8H), 7.97-7.92 (m, 4H), 7.90 (s, 2H), 7.61 (d, J=5.1 Hz, 8H). $^{13}$C NMR (125 MHz, $CDCl_3$) δ 150.6, 150.6, 147.5, 142.3, 140.3, 126.7, 125.5, 121.9. HRMS-ESI (m/z) for TPBP: Calcd for $C_{32}H_{23}N_4^+$: m/z=463.1917 $[M+H]^+$; found 463.1918 $[M+H]^+$.

Scheme 2. Synthesis of TB·4PF$_6$

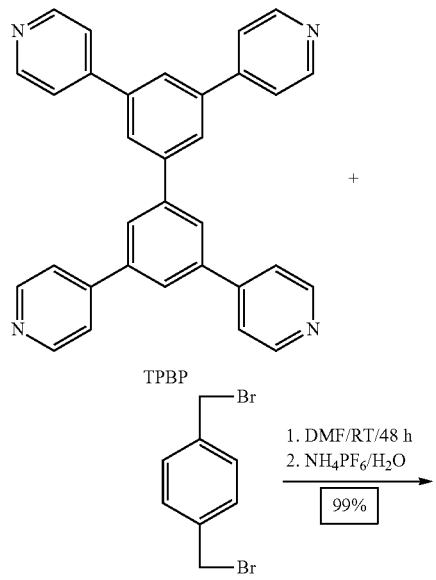

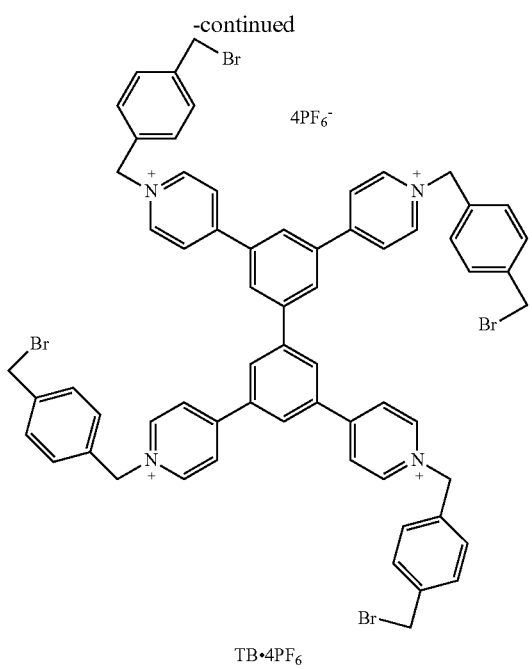

TB·4PF$_6$: TPBP (500 mg, 1.1 mmol) and 1,4-bis(bromomethyl)benzene (6.7 g, 25.4 mmol) were dissolved in anhydrous DMF (500 mL). The reaction mixture was stirred at room temperature for 48 h. $CH_2Cl_2$ (1.5 L) was added and the resulting precipitate was collected by filtration. The precipitate was dissolved in DMF (100 mL), and the insoluble materials were filtered off. $NH_4PF_6$ (2.0 g) was added to the filtrate, followed by addition of $H_2O$ (500 mL) to precipitate out the product TB·4PF$_6$, which was collected by filtration as a white solid (1.9 g, 99% yield). $^1$H NMR (500 MHz, $CD_3CN$) δ 8.91-8.84 (m, 8H), 8.53 (d, J=1.7 Hz, 4H), 8.52-8.48 (m, 8H), 8.41 (s, 2H), 7.55 (d, J=8.2 Hz, 8H), 7.49 (d, J=8.2 Hz, 8H), 5.77 (s, 8H), 4.61 (s, 8H). $^{13}$C NMR (125 MHz, $CD_3CN$) δ 155.9, 145.3, 141.9, 140.8, 136.9, 133.8, 131.1, 130.8, 130.1, 128.7, 126.9, 64.2, 33.2. HRMS-ESI (m/z) for TB·4PF$_6$: Calcd for $C_{64}H_{54}Br_4F_{12}N_4P_2^{2+}$: m/z=744.0167 $[M-2PF_6]^{2+}$; found 744.0170 $[M-2PF_6]^{2+}$.

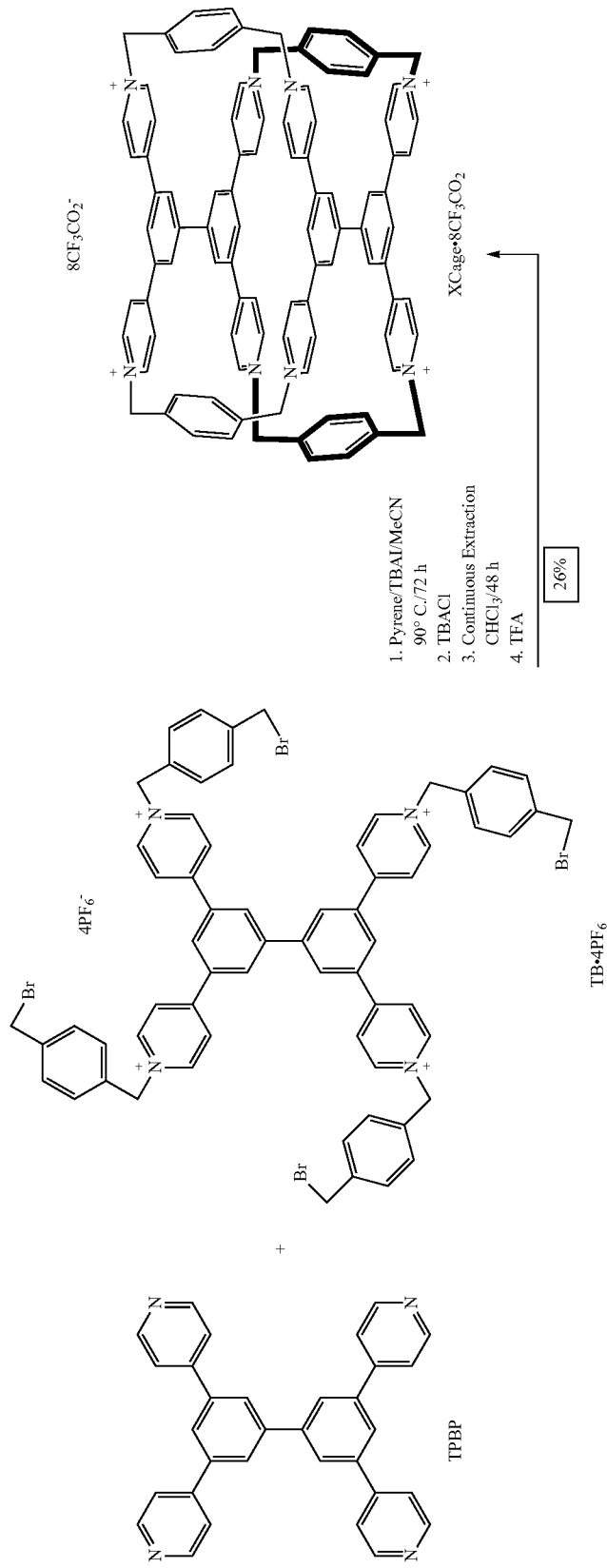

XCage.8CF$_3$CO$_2$: A solution composed of TPBP (120 mg, 0.26 mmol), pyrene (315 mg, 1.60 mmol) and tetrabutylammonium iodide (20 mg, 0.05 mmol) in CHCl$_3$ (20 mL) was added to a solution of TB.4PF$_6$ (450 mg, 0.26 mmol) in MeCN (250 mL). The reaction mixture was heated at 85° C. for 3 days. After cooling to room temperature, tetrabutylammonium chloride (500 mg, 1.8 mmol) and CHCl$_3$ (300 mL) were added to the reaction mixture, the yellow precipitate was isolated by filtration and then dispersed in MeOH (100 mL). Celite (5 g) and TFA (2 mL) were added and the solvent was removed by vacuum. The remaining solid was loaded onto a Combiflash flash chromatography system and purified by reverse Cis columns using 0-25% MeCN/H$_2$O with 0.1% TFA as additive. Fractions containing the product were combined and MeCN was removed by vacuum. The remaining aqueous solution was extracted by continuous liquid-liquid extraction for 48 h until the yellow solution became colorless. H$_2$O was removed and the residue was purified further with reverse C$_{18}$ chromatography using 0-15% MeCN/H$_2$O with 0.1% TFA as additive to obtain the product XCage.8CF$_3$CO$_2$ as a white solid (150 mg, 26% yield).

$^1$H NMR (500 MHz, CD$_3$OD) δ 9.15-9.09 (m, 16H), 8.81 (t, J=2.0 Hz, 8H), 8.66-8.61 (m, 16H), 8.56 (q, J=1.4 Hz, 4H), 7.75 (d, J=2.5 Hz, 16H), 6.00-5.83 (m, 16H). $^{13}$C NMR (125 MHz, CD$_3$OD) δ 159.9, 159.6, 154.4, 144.1, 138.9, 136.4, 135.3, 130.2, 128.6, 127.5, 125.5, 117.1, 114.8, 63.4. HRMS-ESI (m/z) for XCage.8CF$_3$CO$_2$: Calcd for C$_{108}$H$_{76}$F$_{18}$N$_8$O$_{12}$$^{2+}$: m/z=1009.7659 [M-2CF$_3$CO$_2$]$^{2+}$; found 1009.7688 [M-2CF$_3$CO$_2$]$^{2+}$.

Scheme 4. Synthesis of TM·4PF$_6$

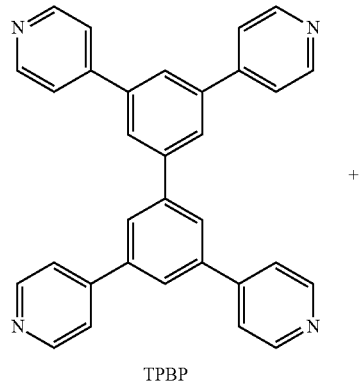

TPBP

1. MeCN/80° C./18 h
2. NH$_4$PF$_6$/H$_2$O

MeI
89%

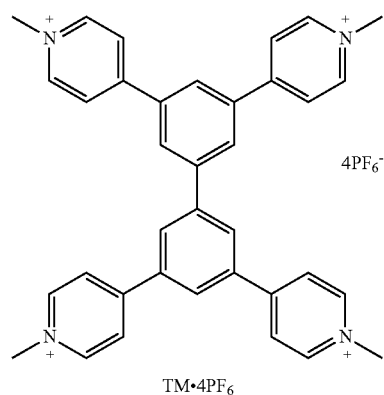

TM·4PF$_6$

TM.4PF$_6$: TPBP (200 mg, 0.43 mmol) and MeI (1.2 g, 8.64 mmol) were suspended in anhydrous MeCN (25 mL). The reaction mixture was heated at 80° C. for 18 h. After cooling to room temperature, CH$_2$Cl$_2$ (100 mL) was added and the resulting precipitate was collected by filtration. H$_2$O (100 mL) was added to dissolve the precipitate, and NH$_4$PF$_6$ (2.0 g) was added to precipitate out the product TM.4PF$_6$ as a yellow solid (420 mg, 89% yield). $^1$H NMR (500 MHz, CD$_3$CN) δ 8.82-8.76 (m, 8H), 8.60 (d, J=1.7 Hz, 4H), 8.57-8.52 (m, 8H), 8.49 (t, J=1.7 Hz, 2H), 4.40 (s, 12H). $^{13}$C NMR (125 MHz, CD$_3$CN) δ 155.1, 146.1, 142.0, 136.9, 130.9, 128.4, 126.2, 48.4. HRMS-ESI (m/z) for TM.4PF$_6$: Calcd for C$_{36}$H$_{34}$F$_{18}$N$_4$P$_3$$^+$: m/z=957.1703 [M-PF$_6$]$^+$; found 957.1716 [M-PF$_6$]$^+$.

Scheme 5. Synthesis of PDI2

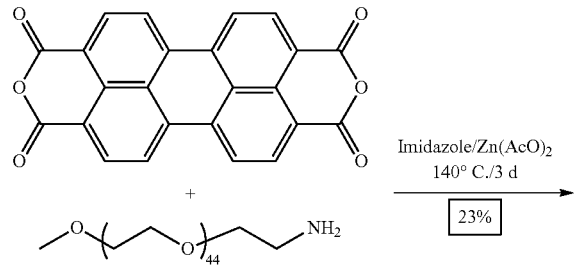

Imidazole/Zn(AcO)$_2$
140° C./3 d
23%

-continued

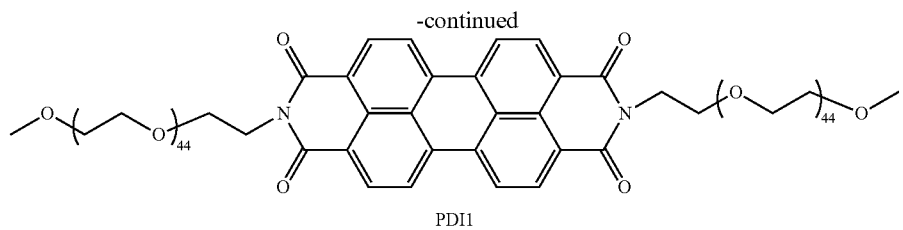

PDI1

PDI2: Perylene-3,4,9,10-tetracarboxylic dianhydride (46.3 mg, 0.118 mmol) and mPEG$_{2000}$-NH$_2$ (500 mg, 0.248 mmol) were added to a mixture of imidazole (2.5 g) and Zn(AcO)$_2$. The reaction mixture was heated at 140° C. under N$_2$ protection for 3 days. After cooling to room temperature, CHCl$_3$ (200 mL) was added to the reaction mixture. The solution was washed with 1 N HCl solution (5×100 mL) and brine (2×100 mL). The organic layer was dried (Na$_2$SO$_4$). The organic solvent was removed, and the residue was purified by column chromatography using 0-10% MeOH/CH$_2$Cl$_2$ with 0.1% NH$_4$OH as additive to obtain the product PDI2 as a dark red solid (120 mg, 23% yield). $^1$H NMR (500 MHz, CDCl$_3$) δ 8.70 (d, J=8.0 Hz, 4H), 8.65 (d, J=8.1 Hz, 4H), 4.47 (s, 4H), 3.86 (t, J=6.1 Hz, 4H), 3.78 (dd, J=5.8, 4.0 Hz, 2H), 3.72 (dd, J=5.8, 3.7 Hz, 4H), 3.64 (d, J=3.3 Hz, 346H), 3.38 (s, 6H). HRMS-ESI (m/z) for PDI2: A cluster peak around 2033 was observed as [M+2Na]$^{2+}$ on account of the polydispersity of PEG chains.

Cyclic Voltammetry

Cyclic voltammetry (CV) was performed at 298 K under a N$_2$ atmosphere with a Gamry Multipurpose instrument (Reference 600) interfaced to a PC. All CV experiments were carried out using a glassy carbon working electrode (0.071 cm$^2$). The electrode surface was polished routinely with 0.05 μm alumina-water slurry on a felt surface immediately before use. The counter electrode was a Pt coil, and the reference electrode was the saturated Ag/AgCl electrode. The concentration of the sample and tetrabutylammonium hexafluoro-phosphate (TBAPF$_6$), were 1.0 mM and 0.1 M, respectively. CV experiments of TM.4PF$_6$ and XCage.8CF$_3$CO$_2$ were conducted at a scan rate of 50 mV/s. The results showed similar behavior with two reduction peaks. Both redox processes are nonreversible, and precipitation developed on electrode after formation of neutral species.

Crystallographic Analysis

Crystal Structure of TPBP (CCDC: 1952500)

(a) Method: TPBP (2 mg) was dissolved in CHCl$_3$ (1 mL), and the solution was passed through a 0.45 μm PTFE filter. The solution was allocated into three culture tubes (each tube containing 250 μL solution). Each cultural tube was then placed in a scintillation vial that contains EtOAc (~3 mL). Slow vapor diffusion of EtOAc into TPBP solution for 4 days yielded colorless crystals of TPBP. A suitable crystal was selected, and the crystal was mounted on a MITIGEN holder with Paratone oil on a Bruker APEX-II CCD diffractometer. The crystal was kept at 100.03 K during data collection. Using Olex2$^{S3}$, the structure was solved with the ShelXD$^{S4}$ structure solution program using Dual Space and refined with the XL$^{S5}$ refinement package using Least Squares minimization.

(b) Crystal Parameters: Empirical formula=C$_{32}$H$_{22}$N$_4$, Formula weight=462.53, monoclinic, space group P2$_1$/c (no. 14), a=14.0428(12), b=10.8941(9), c=16.0875(13) Å, β=113.291(5)°, V=2260.6(3) Å$^3$, Z=4, T=100.03 K, μ(CuKα)=0.634 mm$^{-1}$, D$_{calc}$=1.359 g/mm$^3$, 12620 reflections measured (6.852≤2Θ≤127.35), 3705 unique (R$_{int}$=0.0335, R$_{sigma}$=0.0339) which were used in all calculations. The final R$_1$ was 0.0634 (I>2σ(I)) and wR$_2$ was 0.1751 (all data).

(c) Refinement Details: No special refinement necessary. Crystal Structure of Perylene⊂XCage.8CF$_3$CO$_2$ (CCDC: 1952501)

(a) Method: XCage.8CF$_3$CO$_2$ (2.2 mg, 1 mmol) and perylene (0.5 mg, 2 mmol) was dissolved in MeOH (1 mL), and the solution was passed through a 0.45 μm PTFE filter to obtain Perylene⊂XCage.8CF$_3$CO$_2$ solution. Slow vapor diffusion of isopropyl ether into a Perylene⊂XCage.8CF$_3$CO$_2$ solution for a week yielded yellow crystals of Perylene⊂XCage.8CF$_3$CO$_2$. A suitable crystal was selected, and the crystal was mounted on a MITIGEN holder with Paratone oil on a Bruker APEX-II CCD diffractometer. The crystal was kept at 99.99 K during data collection. Using Olex2$^{S3}$, the structure was solved with the ShelXT$^{S4}$ structure solution program using Intrinsic Phasing and refined with the XL$^{S5}$ refinement package using Least Squares minimization.

(b) Crystal Parameters: Empirical formula=C$_{136}$H$_{104}$F$_{24}$N$_8$O$_{20}$, Formula weight=2626.27, triclinic, space group P-1 (no. 2), a=11.0308(14), b=15.926(2), c=19.347(3) Å, α=99.202(6), β=99.067(6), γ=104.442(6°), V=3179.0(7) Å3, Z=1, T=99.99 K, μ(CuKα)=0.998 mm$^{-1}$, D$_{calc}$=1.372 g/mm$^3$, 36937 reflections measured (4.728≤2Θ≤127.758), 10415 unique (R$_{int}$=0.0399, R$_{sigma}$=0.0384) which were used in all calculations. The final R$_1$ was 0.0536 (I>2σ(I)) and wR$_2$ was 0.1503 (all data).

(c) Refinement Details: The enhanced rigid-bond restraint (SHELX keyword RIGU) was applied on the disordered trifluoroacetate and perylene molecules.$^{S6}$ The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell=321.3 Å$^3$ [10.1%] Total electron count/cell=92.7.

(d) Solvent Treatment Details: No special treatment necessary. (d) Solvent Treatment Details: Not applicable.
Crystal Structure of PDI1⊂XCage.7PF$_6$—OHJ (CCDC: 1952502)

(a) Method: a mixture of XCage.8CF$_3$CO$_2$ (3 mg) and access amounts of PDI1 (20 mg) were mixed in DMF, and the suspension was stirred at 50° C. for 30 min. After cooling to room temperature, the solution was filtrated through a 0.45 μm PTFE filter to remove insoluble PDI1. DMF was then removed by vacuum, and the residue was dissolved in H$_2$O. NH$_4$PF$_6$ was added, and the precipitation was collected by centrifuge to obtain PDI1⊂XCage.8PF$_6$ as a red solid, which was subsequently dissolved in MeCN (1 mL). Slow vapor diffusion of isopropyl ether into a MeCN solution of PDI1 ⊂ XCage.8PF$_6$ for a week yielded pink crystals of PDI1 ⊂ XCage.7PF$_6$·OH. Meanwhile, single crystal of PDI1.2HPF$_6$ was also obtained in the same sample. A suitable crystal was selected, and the crystal was mounted on a MITIGEN holder on a Bruker APEX-II CCD diffractometer. The crystal was kept at 100.0 K during data collection. Using Olex2[S3], the structure was solved with the ShelXD[S4] structure solution program using Dual Space and refined with the XL[S5] refinement package using Least Squares minimization.

(b) Crystal Parameters: Empirical formula=C$_{136}$H$_{118}$F$_{42}$N$_{16}$O$_6$P$_7$, Formula weight=3087.25, tetragonal, space group P4$_3$2$_1$2 (no. 96), a=40.109(4), c=10.8259(13) Å, V=17416(4) Å$^3$, Z=4, T=100.0 K, μ(CuKα)=1.492 mm$^{-1}$, D$_{calc}$=1.177 g/mm$^3$, 37061 reflections measured (3.116≤2Θ≤108.522), 10132 unique (R$_{int}$=0.0658, R$_{sigma}$=0.0634) which were used in all calculations. The final R$_1$ was 0.1051 (I>2σ(I)) and wR$_2$ was 0.2963 (all data).

(c) Refinement Details: The enhanced rigid-bond restraint (SHELX keyword RIGU) was applied globally.[S6] Additionally, isotropic restraints (ISOR) were applied to several ill-behaved atoms on the disordered chains of the substrate molecule. Distance restraints were imposed on the disordered atoms as well as the some of the PF$_6$ anions.

(d) Solvent Treatment Details: The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell=4074.5 Å$^3$ [23.4%]. Total electron count/cell=1026.1.

Crystal Structure of PDI1 (CCDC: 1952502)

(a) Method: Single crystal of PDI1 was co-obtained with PDI1 ⊂ XCage$^{8+}$ crystal sample. A suitable crystal was selected, and the crystal was mounted on a MITIGEN holder with Paratone oil on a Bruker APEX-II CCD diffractometer. The crystal was kept at 100.0 K during data collection. Using Olex2[S3], the structure was solved with the ShelXT[S4] structure solution program using Intrinsic Phasing and refined with the XL[S5] refinement package using Least Squares minimization.

(b) Crystal Parameters: Empirical formula=C$_{32}$H$_{30}$F$_{12}$N$_4$O$_4$P$_2$, Formula weight=824.54, triclinic, space group P-1 (no. 2), a=6.009(2), b=8.492(3), c=16.817(6), α=81.867(7), β=86.681(8), γ=71.757(7)°, V=806.7(5) Å$^3$, Z=1, T=100.0 K, μ(MoKα)=0.252 mm$^{-1}$, D$_{calc}$=1.697 g/mm$^3$, 9396 reflections measured (2.446≤2Θ≤52.588), 3201 unique (R$_{int}$=0.0583, R$_{sigma}$=0.0781) which were used in all calculations. The final R$_1$ was 0.0471 (I>2σ(I)) and wR$_2$ was 0.1135 (all data).

(c) Refinement Details: No special refinement necessary.

(d) Solvent Treatment Details: Not applicable.

Electrostatic Potential Map Calculation

The Cartesian coordinates of single crystal structure of PDI were modified as initial input and optimized by Gaussian 16 at B3LYP/6-31G* level.[S7] The out-put files were used further to calculate electron static potential maps by GaussView.[S8]

Surface-Area Overlap (SAO) Analysis

Surface-area overlap analysis was performed by Chimera and Image J software. Single crystal structures of the receptor-substrate complex were truncated by removing the top half of XCage$^{8+}$ and visualized by Chimera.[S9] The substrates and XCage$^{8+}$ receptor were colored to show the bridging units (2), the binding cavity of the receptor (1), the area of substrate (3), and the overlapping portion between the receptor and substrate (4). ImageJ 1.49 software was used to measure the percent of SAO in each receptor-substrate complex.[S10] Values were calculated for the SAO-XCage (the overlapping portion between the receptor and substrate divided by the total area of the receptor) and SAO-substrate (the overlapping portion between the receptor and substrate divided by the total area of the substrate).[S11]

The Cartesian coordinates of the single crystal structure of Perylene ⊂ XCage$^{8+}$ was modified by removing perylene substrate, and the resulting empty XCage$^{8+}$ was then analyzed by Multiwfn program 3.6 program[S11] to calculate the cavity volume through the domain analysis function.

Independent Gradient Model Analysis

Independent gradient model (IGM) analysis is an approach based on pro-molecular density to identify and isolate intermolecular interactions.[S12] Hydrogen bonds and van der Waals contacts are visualized as an iso-surface with blue and green color respectively. Single crystal structures of the receptor-substrate complexes were used as input file. The binding surface was calculated by Multiwfn 3.6 program[S11] through function 20 (visual study of weak interaction) and visualized by Chimera program.

Photophysical Characterization

The fluorescence quantum yield of PDI dyes were measured by using rhodamine 6G in EtOH (Φ$_f$=0.95) as standard.[S2] The concentrations of rhodamine 6G and PDI dyes were adjusted to the absorption value 0.08 at 450 nm. The fluorescence spectrum of each solution was obtained with excitation at 450 nm, and the integrated area was used in the fluorescence quantum yield calculation. The estimated error for this method[S13] is ±10%. The fluorescent life-time was measured by Horiba Fluoromax-4 fluorometer equipped with TCSPC. Samples were excited by a laser at 374 nm, and the fluorescence decay over time was monitored at 560 nm. The fluorescent decay profiles were analyzed by a DAS6 software and matched either by a single exponential decay or double exponential decay model through mathematic fittings. Tables 2 and 3 summarize the photophysical properties in H$_2$O and MeCN.

Binding Studies by Fluorescence

In all experiments shown below, ExBox.4Cl and XCage.8CF$_3$CO$_2$ were used in titration studies. Here we use ExBox$^{4+}$ and XCage$^{8+}$ for short. All of the solutions were prepared in spectroscopic grade solvents and equilibrated for 24 h at room temperature before use. All of the studies were independently duplicated and the corresponding isotherms were fitted to calculate the average K$_a$ or k$_{on}$ values with the relevant standard errors. All of the titrations were performed at 25° C., and the corresponding Gibbs free energy was determined from K$_a$.

Determination of Binding Constants

Direct fluorescence titration experiments: Since the association between PDI2 and ExBox$^{4+}$ in H$_2$O produces turn-on fluorescence, we tracked the increase of fluorescence (ex:

545 nm, em: 555 nm) of PDI2 by varying equivalents of ExBox$^{4+}$. Caffeine is not fluorescent in H$_2$O and its association with XCage$^{8+}$ quenches the fluorescence of XCage$^{8+}$. Thus, the fluorescence quenching of XCage$^{8+}$ was tracked by the addition of Caffeine. In MeCN, the fluorescence of perylene is quenched by XCage$^{8+}$ and thus the titration was performed by tracking the fluorescence quenching of Perylene. A plot of fluorescent intensity versus receptor concentration [R]$_0$ or substrate concentration [S]$_0$ was fitted with a nonlinear least-squares fitting equation for 1:1 binding model to calculate the binding constant K$_a$ using Origin Lab 8.6 software.$^{S14, S15}$ Displacement fluorescence titration experiments in H$_2$O: A large access of the competitor caffeine (10 mM) was pre-mixed with XCage$^{8+}$ (10 µM), and the solution was equilibrated for 30 min before titration. The substrate solution of PDI2 was injected in aliquots. For each injection, the guest displacement process was relatively slow and took about 3-10 min to reach the equilibrium as monitored by the change of fluorescence (ex: 560 nm, em: 660 nm) over time. At this excitation wavelength, PDI2 ⊂ XCage$^{8+}$ is fluorescent; XCage$^{8+}$, PDI2 and Caffeine are nonfluorescent. The association constants were calculated by fitting the titration data with a nonlinear least-squares fitting equation for displacement binding using Origin Lab 8.6 software.$^{S14}$ Displacement fluorescence titration experiments in MeCN: Perylene (250 µM) was premixed with XCage$^{8+}$ (5 µM) in MeCN, and the solution was equilibrated for 30 min before titration. The substrate solution of PDI2 was injected in aliquot amount. Between each injection, the change of fluorescence intensity was monitored over time until the fluorescence (ex: 550 nm, em: 660 nm) intensity reached a steady state. At this excitation wavelength, PDI2↑XCage$^{8+}$ is fluorescent while XCage$^{8+}$ and PDI2 are nonfluorescent. The association constants were calculated by fitting the titration data with a nonlinear least-squares fitting equation for displacement binding using Origin Lab 8.6 software.$^{S14}$ Determination of Binding Kinetics Equal volume of PDI2 (1 µL, 100 µM) and XCage$^{8+}$ (1 µL, 100 µM) were mixed in H$_2$O (1 mL) and the change of fluorescence (ex: 540 nm, em: 554 nm) was monitored over time. The resulting threading kinetics profiles were fitted using a second order kinetics model by Origin Lab 8.6 software. In MeCN, the change of fluorescence over time upon the formation of PDI2 ⊂ XCage$^{8+}$ is too small to produce a kinetics profile as a result of the similar quantum yield between PDI2 ⊂ XCage$^{8+}$ and PDI2.

Isothermal Titration Calorimetry (ITC)

In all ITC experiments, ExBox.4Cl and XCage.8CF$_3$CO$_2$ were used in titrations. Here we use ExBox$^{4+}$ and XCage$^{8+}$ for short. All of the solutions were prepared in spectroscopic grade solvents and equilibrated for 24 h at room temperature before use. All of the titrations were independently duplicated—shown below is one set of titration isotherms—and all isotherm fittings were used to calculate the average K$_a$ and ΔH with relevant standard errors.

Isothermal titration was performed by TA Nano Isothermal Titration Calorimeter at 25° C. A hastelloy cell was used with an active cell volume 190 µL. The stirring speed was set at 150 rpm. Receptor and substrate solutions were prepared in Milli-Q water or MeCN and allowed to equilibrate overnight if necessary. In each titration experiment, 20-25 injections were performed with gradually decreased titration peaks until saturation is reached, at which point only heat of dilution was measured. After subtracting the heat of dilution, the resulting data were analyzed with NanoAnalyze software using a 1:1 binding model and plotted by Origin Lab 8.6 software.

Cell Imaging Studies

For all cell imaging experiments, XCage.8CF$_3$CO$_2$ was supplied for cell study; we use XCage$^{8+}$ for short.

Cell Culture

MCF-7 cells (human breast adenocarcinoma cell line) obtained from American Type Culture Collection (ATCC, Rockville, Md., USA) was utilized for cell culture experiments. MCF-7 cells were cultured in Dulbecco's Modified Eagle's Medium (DMEM) supplemented with 10% fetal bovine serum (FBS), penicillin (100 IU/mL) and streptomycin (100 µg/mL) at 37° C. in the presence of air (95%) and carbon dioxide (5%).

MTT Assay

MCF-7 cells (2.5×10$^5$ cells/ml, 100 µL) were seeded in each well of a flat bottomed 96-well plate and adhered overnight. PDI2 or PDI2 ⊂ XCage$^{8+}$ or XCage$^{8+}$ in PBS (10 µL) was added to each well to achieve working concentrations and incubated for 24 h. After incubation, wells were washed with PBS and incubated with MTT (0.5 mg/ml in DMEM, 100 µL) for 4 h. Following incubation with MTT, media from each well was aspirated, and the resultant formazan crystals deposited on the plate were dissolved in 200 µL of dimethyl sulfoxide. Then the absorbance of each well was measured using a microplate reader at 560 nm. All the samples were analyzed in quadruplicates. The percentage cell viability was then calculated using the formula % cell viability=(OD of treated sample/OD of untreated sample)*100.

Cell Uptake Studies

MCF-7 cells (2×10$^5$ cells/ml, 500 µL) were seeded in each well of a 24-well plate and adhered overnight. For time dependent uptake studies, each well was treated with 10 µM PDI2, XCage$^{8+}$ or PDI2 ⊂ XCage$^{8+}$ or for 30 min, 1 h, 2 h, 4 h, or 6 h. For concentration dependent uptake studies, each well was treated 0.1 or 1 or 10 or 20 µM of PDI2 ⊂ XCage$^{8+}$ for 6 h. After each incubation, cells were washed twice with 1×PBS, trypsinized, and incubated with 50 µL of 1:100 Zombie Aqua fixable cell viability dye for 20 min at 4° C. Further cells were washed with 600 µL 1×PBS, spun at 400 relative centrifugal forces (rcf) for 5 min and cell pellets were resuspended in 200 µL of 2% paraformaldehyde prior to being analyzed using a BD Fortessa flow cytometer. Data analysis was performed using Cytobank software (Cytobank Inc). Cells were first gated for singlet events using FSC-A vs FSC-H, after which debris was excluded used FSC-A vs SSC-A. Cells gated as Zombie Aqua low were considered live cells, which were then analyzed for their median fluorescence intensity (MFI) in the PE-Cy5 channel for PDI2 ⊂ XCage$^{8+}$ fluorescence, representing the amount of PDI2 ⊂ XCage$^{8+}$ taken up by each cell.

Live Cell Confocal and Widefield Microscopy

MCF-7 cells (1×10$^5$ cells/ml, 300 µL) were plated in each well of an 8-well chamber slide (ThermoFischer Scientific)

and adhered overnight. PDI2 or PDI2 ⊂ XCage$^{8+}$ was added to each well and incubated for 6 h or 24 h. Cells were then washed with PBS, and stained with LysoTracker green (lysosome stain, 1:1000 dilution) or NucBlue™ Live Ready-Probes™ Reagent (nuclear stain, 1 drop) or Hoechst 33342 nucleic acid stain (1:2000 dilution from 10 mg/mL stock). Plated cells were imaged within a humidified chamber using a 63× oil-immersion objective on a SP5 Leica Confocal Microscope using HyD detectors and lasers or a Deltavision Core Elite with a DAPI excitation filter (381-399 nm), DAPI emission filter (em: 411-459 nm) and TRITC emission filter (em: 571-617 nm) at equivalent light levels and exposure time. Intensity of signal in cells was measured with FIJI/ImageJ software.

TABLES

TABLE 1

Binding Constants and Thermodynamic Data at 25° C.$^a$

| Entry | Solvent | Guest | Fluorescence Ka/M$^{-1}$ | ITC Ka/M$^{-1}$ | ΔG (kcal mol$^{-1}$) | ΔH (kcal mol$^{-1}$) | TΔS (kcal mol$^{-1}$) |
|---|---|---|---|---|---|---|---|
| 1 | MeCN | Perylene | 5.0 × 10$^6$ | 3.6 × 10$^6$ | −08.9$^c$ | −06.9 | 2.0 |
| 2 | MeCN | PDI2 | 3.5 × 10$^9$ | ND$^b$ | −13.0$^d$ | −10.2 | 2.8 |
| 3 | H$_2$O | Caffeine | 1.2 × 10$^5$ | 1.5 × 10$^5$ | −7.1$^c$ | −8.6 | −1.5 |
| 4 | H$_2$O | PDI2 | 7.7 × 10$^{10}$ | ND$^b$ | −14.8$^d$ | −14.1 | 0.7 |

$^a$The standard error is presented in Supporting Information.
$^b$Not determined.
$^c$Directly determined by ITC.
$^d$Estimated from fluorescence titrations

TABLE 2

Summary of Photophysical Properties in H$_2$O

| Compound | PDI2 | PDI2 ⊂ XCage$^{8+}$ |
|---|---|---|
| $\lambda_{abs}$ (nm) | 497/534 | 472/504/542 |
| $\lambda_{ex}$ (nm) | 461/502/529 | 470/502/540 |
| $\lambda_{em}$ (nm) | 542/586/633 | 554/598/648 |
| logε | 4.48 | 4.65 |
| $\Phi_f$ | 0.04 | 0.63 |
| τ (ns) | 4.71 | 7.32 |

TABLE 3

Summary of Photophysical Properties in MeCN

| Compound | PDI2 | PDI2 ⊂ XCage$^{8+}$ |
|---|---|---|
| $\lambda_{abs}$ (nm) | 456/484/520 | 472/504/543 |
| $\lambda_{ex}$ (nm) | 452/482/518 | 474/505/542 |
| $\lambda_{em}$ (nm) | 529/568/617 | 553/597/649 |
| logε | 4.91 | 4.71 |
| $\Phi_f$ | 0.66 | 0.66 |
| τ (ns) | 4.47 | 3.30/8.34 |

REFERENCES (1) Szwajkajzer, D.; Carey, J. Molecular and Biological Constraints on Ligand-Binding Affinity and Specificity. *Biopolymers* 1997, 44, 181-198.

(2) Persch, E.; Dumele, O.; Diederich, F. Molecular Recognition in Chemical and Biological Systems. *Angew. Chem. Int. Ed.* 2015, 54, 3290-3327.

(3) Cremer, P. S.; Flood, A. H.; Gibb, B. C.; Mobley, D. L. Collaborative Routes to Clarifying The Murky Waters of Aqueous Supramolecular Chemistry. *Nat. Chem.* 2017, 10, 8-16.

(4) Liu, Y.; Zhao, W.; Chen, C.-H.; Flood, A. H. Chloride Capture Using a C—H Hydrogen Bonding Cage. *Science.* 2019, 365, 159-161.

(5) Tromans, R. A.; Carter, T. S.; Chabanne, L.; Crump, M. P.; Li, H.; Matlock, J. V.; Orchard, M. G.; Davis, A. P. A Biomimetic Receptor for Glucose. *Nat. Chem.* 2019, 11, 52-56.

(6) Houk, K. N.; Leach, A. G.; Kim, S. P.; Zhang, X. Binding Affinities of Host-Guest, Protein-Ligand, and Protein-Transition-state Complexes. *Angew. Chem. Int. Ed.* 2003, 42, 4872-4897.

(7) Shetty, D.; Khedkar, J. K.; Park, K. M.; Kim, K. Can We Beat The Biotin-Avidin Pair?: Cucurbit[7]uril-Based Ultrahigh Affinity Host-Guest Complexes and Their Applications. *Chem. Soc. Rev.* 2015, 44, 8747-8761.

(8) Assaf, K. I.; Nau, W. M. Cucurbiturils: From Synthesis to High-Affinity Binding and Catalysis. *Chem. Soc. Rev.* 2015, 44, 394-418.

(9) Barrow, S. J.; Kasera, S.; Rowland, M. J.; Del Barrio, J.; Scherman, O. A. Cucurbituril-Based Molecular Recognition. *Chem. Rev.* 2015, 115, 12320-12406.

(10) Ogoshi, T.; Yamagishi, T. A.; Nakamoto, Y. Pillar-Shaped Macrocyclic Hosts Pillar[n]arenes: New Key Players for Supramolecular Chemistry. *Chem. Rev* 2016, 116, 7937-8002.

(11) Li, D.-H.; Smith, B. D. Molecular Recognition Using Tetralactam Macrocycles with Parallel Aromatic Sidewalls. Beilstein *J. Org. Chem.* 2019, 15, 1086-1095.

(12) Liu, W.; Samanta, S. K.; Smith, B. D.; Isaacs, L. Synthetic Mimics of Biotin/(Strept)Avidin. *Chem. Soc. Rev.* 2017, 46, 2391-2403.

(13) Schreiber, C. L.; Smith, B. D. Molecular Conjugation Using Non-Covalent Click Chemistry. *Nat. Rev. Chem.* 2019, 3, 393-400.

(14) Mako, T. L.; Racicot, J. M.; Levine, M. Supramolecular Luminescent Sensors. *Chem. Rev.* 2019, 119, 322-477.

(15) Heinzmann, C.; Weder, C.; de Espinosa, L. M. Supramolecular Polymer Adhesives: Advanced Materials Inspired by Nature. *Chem. Soc. Rev.* 2015, 342, 342-358.

(16) Wang, H.; Ji, X.; Li, Z.; Huang, F. Fluorescent Supramolecular Polymeric Materials. *Adv. Mater.* 2017, 29, 1606117.

(17) Ariga, K.; Li, J.; Fei, J.; Ji, Q.; Hill, J. P. Nanoarchitectonics for Dynamic Functional Materials from Atomic-/Molecular-Level Manipulation to Macroscopic Action. *Adv. Mater.* 2016, 28, 1251-1286.

(18) Pan, J.; Chen, W.; Ma, Y.; Pan, G. Molecularly Imprinted Polymers as Receptor Mimics for Selective Cell Recognition. *Chem. Soc. Rev.* 2018, 47, 5574-5587.

(19) Sarikaya, M.; Tamerler, C.; Jen, A. K.-Y.; Schulten, K.; Baneyx, F. Molecular Biomimetics: Nanotechnology through Biology. *Nat. Mater.* 2003, 2, 577-585.

(20) Webber, M. J.; Langer, R. Drug Delivery by Supramolecular *Design. Chem. Soc. Rev.* 2017, 46, 6600-6620.

(21) Murray, J.; Kim, K.; Ogoshi, T.; Yao, W.; Gibb, B. C. The Aqueous Supramolecular Chemistry of Cucurbit[n]urils, Pillar[n]Arenes and Deep-Cavity Cavitands. *Chem. Soc. Rev.* 2017, 46, 2479-2496.

(22) Chodera, J. D.; Mobley, D. L. Entropy-Enthalpy Compensation: Role and Ramifications in Biomolecular Ligand Recognition and Design. *Annu. Rev. Biophys.* 2013, 42, 121-142.

(23) Rekharsky, M. V; Mori, T.; Yang, C.; Ko, Y. H.; Selvapalam, N.; Kim, H.; Sobransingh, D.; Kaifer, A. E.; Liu, S.; Isaacs, L.; et al. A Synthetic Host-Guest System Achieves Avidin-Biotin Affinity by Overcoming Enthalpy-Entropy Compensation. *Proc. Natl. Acad. Sci. U.S.A.* 2007, 104, 20737-20742.

(24) Liu, W.; Johnson, A.; Smith, B. D. Guest Back-Folding: A Molecular Design Strategy That Produces a Deep-Red Fluorescent Host/Guest Pair with Picomolar Affinity in Water. *J. Am. Chem. Soc.* 2018, 140, 3361-3370.

(25) Spenst, P.; Würthner, F. A Perylene Bisimide Cyclophane as a "Turn-On" and "Turn-Off" Fluorescence Probe. *Angew. Chem. Int. Ed.* 2015, 54, 10165-10168.

(26) Sapotta, M.; Hofmann, A.; Bialas, D.; Würthner, F. A Water-Soluble Perylene Bisimide Cyclophane as A Molecular Probe for The Recognition of Aromatic Alkaloids. *Angew. Chem. Int. Ed.* 2019, 58, 3516-3520.

(27) Dale, E. J.; Vermeulen, N. A.; Jurifek, M.; Barnes, J. C.; Young, R. M.; Wasielewski, M. R.; Stoddart, J. F. Supramolecular Explorations: Exhibiting The Extent of Extended Cationic Cyclophanes. *Acc. Chem. Res.* 2016, 49, 262-273.

(28) Barnes, J. C.; Jurifek, M.; Strutt, N. L.; Frasconi, M.; Sampath, S.; Giesener, M. A.; McGrier, P. L.; Bruns, C. J.; Stern, C. L.; Sarjeant, A. A.; et al. ExBox: A Polycyclic Aromatic Hydrocarbon Scavenger. *J. Am. Chem. Soc.* 2013, 135, 183-192.

(29) Dale, E. J.; Vermeulen, N. A.; Thomas, A. A.; Barnes, J. C.; Jurifek, M.; Blackburn, A. K.; Strutt, N. L.; Sarjeant, A. A.; Stern, C. L.; Denmark, S. E.; et al. ExCage. *J. Am. Chem. Soc.* 2014, 136, 10669-10682.

(30) Tsutsui, T.; Kusaba, S.; Yamashina, M.; Akita, M.; Yoshizawa, M. Open Versus Closed Polyaromatic Nanocavity: Enhanced Host Abilities toward Large Dyes and Pigments. *Chem. Eur. J* 2019, 25, 4320-4324.

(31) Yoshizawa, M.; Catti, L. Bent Anthracene Dimers as Versatile Building Blocks for Supramolecular Capsules. *Acc. Chem. Res.* 2019, 52, 2392-2404.

(32) Yamashina, M.; Tsutsui, T.; Sei, Y.; Akita, M.; Yoshizawa, M. A Polyaromatic Receptor with High Androgen Affinity. *Sci. Adv.* 2019, 5, 1-8.

(33) Jono, K.; Suzuki, A.; Akita, M.; Albrecht, K.; Yamamoto, K.; Yoshizawa, M. A Polyaromatic Molecular Clip That Enables the Binding of Planar, Tubular, and Dendritic Compounds. *Angew. Chem. Int. Ed.* 2017, 56, 3570-3574.

(34) Yamauchi, Y.; Yoshizawa, M.; Akita, M.; Fujita, M. Engineering Double to Quintuple Stacks of a Polarized Aromatic in Confined Cavities. *J. Am. Chem. Soc.* 2010, 132, 960-966.

(35) Würthner, F.; Saha-Möller, C. R.; Fimmel, B.; Ogi, S.; Leowanawat, P.; Schmidt, D. Perylene Bisimide Dye Assemblies as Archetype Functional Supramolecular Materials. *Chem. Rev.* 2016, 116, 962-1052.

(36) Sun, M.; Müllen, K.; Yin, M. Water-Soluble Perylenediimides: Design Concepts and Biological Applications. *Chem. Soc. Rev.* 2016, 45, 1513-1528.

(37) Ryan, S. T. J.; Del Barrio, J.; Ghosh, I.; Biedermann, F.; Lazar, A. I.; Lan, Y.; Coulston, R. J.; Nau, W. M.; Scherman, O. A. Efficient Host-Guest Energy Transfer in Polycationic Cyclophane-Perylene Diimide Complexes in Water. *J. Am. Chem. Soc.* 2014, 136, 9053-9060.

(38) Biedermann, F.; Elmalem, E.; Ghosh, I.; Nau, W. M.; Scherman, O. A. Strongly Fluorescent, Switchable Perylene Bis(Diimide) Host-Guest Complexes with Cucurbit[8]uril in Water. *Angew. Chem. Int. Ed.* 2012, 51, 7739-7743.

(39) Barnes, J. C.; Jurifek, M.; Vermeulen, N. A.; Dale, E. J.; Stoddart, J. F. Synthesis of Ex"Box Cyclophanes. *J. Org. Chem.* 2013, 78, 11962-11969.

(44) Nau, W. M.; Florea, M.; Assaf, K. I. Deep Inside Cucurbiturils: Physical Properties and Volumes of Their Inner Cavity Determine The Hydrophobic Driving Force for Host-Guest Complexation. *Isr. J. Chem.* 2011, 51, 559-577.

(45) Lefebvre, C.; Rubez, G.; Khartabil, H.; Boisson, J. C.; Contreras-Garcia, J.; Hénon, E. Accurately Extracting The Signature of Intermolecular Interactions Present in The NCI Plot of The Reduced Density Gradient Versus Electron Density. *Phys. Chem. Chem. Phys.* 2017, 19, 17928-17936.

(46) Lu, T.; Chen, F. Multiwfn: A Multifunctional Wavefunction Analyzer. *J. Comput. Chem.* 2012, 33, 580-592.

(47) Cao, L.; Sekutor, M.; Zavalij, P. Y.; Mlinaric-Majerski, K.; Glaser, R.; Isaacs, L. Cucurbit[7]uril. Guest Pair with an Attomolar Dissociation Constant. *Angew. Chem., Int. Ed.* 2014, 53, 988-993.

(48) Ryan, S. T. J.; Young, R. M.; Henkelis, J. J.; Hafezi, N.; Vermeulen, N. A.; Hennig, A.; Dale, E. J.; Wu, Y.; Krzyaniak, M. D.; Fox, A.; et al. Energy and Electron Transfer Dynamics within a Series of Perylene Diimide/Cyclophane Systems. *J. Am. Chem. Soc.* 2015, 137, 15299-15307.

(50) Ringe, D.; Petsko, G. A. How Enzymes Work. *Science.* 2008, 320, 1428-1429.

(53) Heek, T.; Fasting, C.; Rest, C.; Zhang, X.; Würthner, F.; Haag, R. Highly Fluorescent Water-Soluble Polyglycerol-Dendronized Perylene Bisimide Dyes. *Chem. Commun.* 2010, 46, 1884-1886.

(55) Ishida, T.; Morisaki, Y.; Chujo, Y. Synthesis of Covalently Bonded Nanostructure from Two Porphyrin Molecular Wires Leading to a Molecular Tube. *Tetrahedron Lett.* 2006, 47, 5265-5268.

(56) Yamashina, M.; Kusaba, S.; Akita, M.; Kikuchi, T.; Yoshizawa, M. Cramming Versus Threading of Long Amphiphilic Oligomers into a Polyaromatic Capsule. *Nat. Commun.* 2018, 9, 3-9.

(57) Deutman, A. B. C.; Monnereau, C.; Elemans, J. a a W.; Ercolani, G.; Nolte, R. J. M.; Rowan, A. E. Mechanism of Threading a Polymer through a Macrocyclic Ring. *Science.* 2008, 322, 1668-1671.

(59) Biedermann, F.; Nau, W. M.; Schneider, H. J. The Hydrophobic Effect Revisited—Studies with Supramolecular Complexes Imply High-Energy Water as a Noncovalent Driving Force. *Angew. Chem. Int. Ed.* 2014, 53, 11158-11171.

(60) Gibb, B. C. Supramolecular Assembly and Binding in Aqueous Solution: Useful Tips Regarding The Hofmeister and Hydrophobic Effects. *Isr. J. Chem.* 2011, 51, 798-806.

(61) Fan, J.; Hu, M.; Zhan, P.; Peng, X. Energy Transfer Cassettes Based on Organic Fluorophores: Construction and Applications in Ratiometric Sensing. *Chem. Soc. Rev.* 2013, 42, 29-43.

(62) Chu, J.; Oh, Y.; Sens, A.; Ataie, N.; Dana, H.; Macklin, J. J.; Laviv, T.; Welf, E. S.; Dean, K. M.; Zhang, F.; et al. A Bright Cyan-Excitable Orange Fluorescent Protein Facilitates Dual-Emission Microscopy and Enhances Bioluminescence Imaging in Vivo. *Nat. Biotechnol.* 2016, 34, 760-767.

(63) Garwin, S. A.; Kelley, M. S. J.; Sue, A. C.; Que, E. L.; Schatz, G. C.; Woodruff, T. K.; O'Halloran, T. V. Interrogating Intracellular Zinc Chemistry with a Long Stokes Shift Zinc Probe ZincBY-4. *J. Am. Chem. Soc.* 2019, 141, 16696-16705.

(64) Kogure, T.; Karasawa, S.; Araki, T.; Saito, K.; Kinjo, M.; Miyawaki, A. A Fluorescent Variant of a Protein from The Stony Coral Montipora Facilitates Dual-Color Single-Laser Fluorescence Cross-Correlation Spectroscopy. *Nat. Biotechnol.* 2006, 24, 577-581.

(65) Butkevich, A. N.; Lukinavicius, G.; D'Este, E.; Hell, S. W. Cell-Permeant Large Stokes Shift Dyes for Transfection-Free Multicolor Nanoscopy. *J. Am. Chem. Soc.* 2017, 139, 12378-12381.

(66) Sednev, M. V.; Belov, V. N.; Hell, S. W. Fluorescent Dyes with Large Stokes Shifts for Super-Resolution Optical Microscopy of Biological Objects: A Review. *Methods Appl. Fluoresc.* 2015, 3, 042004.

(67) Weil, T.; Vosch, T.; Hofkens, J.; Peneva, K.; Mullen, K. The Rylene Colorant Family-Tailored Nanoemitters for Photonics Research and Applications. *Angew. Chem. Int. Ed.* 2010, 49, 9068-9093.

(68) Li, X.; Hihath, J.; Chen, F.; Masuda, T.; Zang, L.; Tao, N. Thermally Activated Electron Transport in Single Redox Molecules. *J. Am. Chem. Soc.* 2007, 129, 11535-11542.

(69) Xu, B.; Xiao, X.; Yang, X.; Zang, L.; Tao, N. Large Gate Modulation in The Current of a Room Temperature Single Molecule Transistor. *J. Am. Chem. Soc.* 2005, 127, 2386-2387.

(70) Xin, N.; Guan, J.; Zhou, C.; Chen, X.; Gu, C.; Li, Y.; Ratner, M. A.; Nitzan, A.; Stoddart, J. F.; Guo, X. Concepts in The Design and Engineering of Single-Molecule Electronic Devices. *Nat. Rev. Phys.* 2019, 1, 211-230.

S1. Jiao, Y., Liu, K., Wang, G., Wang, Y., and Zhang, X. Supramolecular Free Radicals: Near-Infrared Organic Materials with Enhanced Photothermal Conversion. *Chem. Sci.* 2015, 6, 3975-3980.

S2. Ryan, S. T. J., Del Barrio, J., Ghosh, I., Biedermann, F., Lazar, A. I., Lan, Y., Coulston, R. J., Nau, W. M., and Scherman, O. A. Efficient Host-Guest Energy Transfer in Polycationic Cyclophane-Perylene Diimide Complexes in Water. *J. Am. Chem. Soc.* 2014, 136, 9053-9060.

S3. Dolomanov, O. V, Bourhis, L. J., Gildea, R. J., Howard, J. A. K., and Puschmann, H. OLEX2: A Complete Structure Solution, Refinement and Analysis Program. *J. Appl. Crystallogr.* 2009, 42, 339-341.

S4. Sheldrick, G. M. SHELXT-Integrated Space-Group and Crystal-Structure Determination. *Acta Crystallogr. Sect. A.* 2015, 71, 3-8.

S5. Sheldrick, G. M. A Short History of SHELX. *Acta Crystallogr. Sect. A.* 2008, 64, 112-122.

S6. Thorn, A., Dittrich, B., and Sheldrick, G. M. Enhanced Rigid-Bond Restraints. *Acta Crystallogr. Sect. A.* 2012, 68, 448-451.

S7. Frisch, M. J., Trucks, G. W., Schlegel, H. B., Scuseria, G. E., Robb, M. A., Cheeseman, J. R., Scalmani, G., Barone, V., Petersson, G. A., Nakatsuji, H., et al. 2016, Gaussian 16.

S8. Dennington, R., Keith, T. A., and Millam, J. M. 2019, GaussView, Version 6.1.

S9. Pettersen, E. F., Goddard, T. D., Huang, C. C., Couch, G. S., Greenblatt, D. M., Meng, E. C., and Ferrin, T. E. UCSF Chimera—A Visualization System for Exploratory Research and Analysis. *J. Comput. Chem.* 2004, 25, 1605-1612.

S10. Schneider, C. A., Rasband, W. S., and Eliceiri, K. W. NIH Image to ImageJ: 25 Years of Image Analysis. *Nat. Methods* 2012, 9, 671-675.

S11. Dale, E. J., Vermeulen, N. A., Thomas, A. A., Barnes, J. C., Juricek, M., Blackburn, A. K., Strutt, N. L., Sarjeant, A. A., Stern, C. L., Denmark, S. E., et al. ExCage. *J. Am. Chem. Soc.* 2014, 136, 10669-10682.

S12. Lefebvre, C., Rubez, G., Khartabil, H., Boisson, J. C., Contreras-Garcia, J., and Hénon, E. Accurately Extracting the Signature of Intermolecular Interactions Present in The NCI Plot of The Reduced Density Gradient Versus Electron Density. *Phys. Chem. Chem. Phys.* 2017, 19, 17928-17936.

S13. Brouwer, A. M. Standards for Photoluminescence Quantum Yield Measurements in Solution (IUPAC Technical Report). *Pure Appl. Chem.* 2011, 83, 2213-2228.

S14. Hargrove, A. E., Zhong, Z., Sessler, J. L., and Anslyn, E. V. Algorithms for The Determination of Binding Constants and Enantiomeric Excess in Complex Host: Guest Equilibria Using Optical Measurements. *New J Chem.* 2010, 34, 348-354.

S15. Thordarson, P. Determining Association Constants from Titration Experiments in Supramolecular Chemistry. *Chem. Soc. Rev.* 2011, 40, 1305-23.

S16. Rekharsky, M. V; Mori, T.; Yang, C.; Ko, Y. H.; Selvapalam, N.; Kim, H.; Sobransingh, D.; Kaifer, A. E.; Liu, S.; Isaacs, L.; et al. A Synthetic Host-Guest System Achieves Avidin-Biotin Affinity by Overcoming Enthalpy-Entropy Compensation. *Proc. Nat. Acad. Sci. U.S.A.* 2007, 104, 20737-20742.

We claim:

1. A tricyclic octacationic cyclophane or a salt thereof, the cyclophane comprising a roof, a floor, and four pillars, wherein each of the roof and the floor are composed of a biphenyl unit having four pyridinium units extending therefrom and wherein each of the four pyridinium units of the roof are linked to another pyridinium unit of the floor by one of the four pillars.

2. The cyclophane of claim 1, wherein the cyclophane is

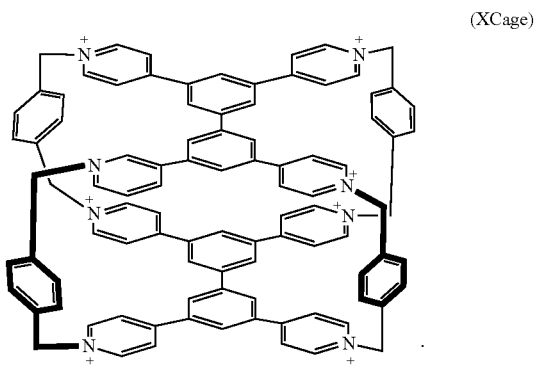

(XCage)

3. A receptor-substrate complex, the complex comprising the tricyclic octacationic cyclophane according to claim 1 and a perylene diimide dye complexed therein.

4. The complex of claim 3, wherein the cyclophane is

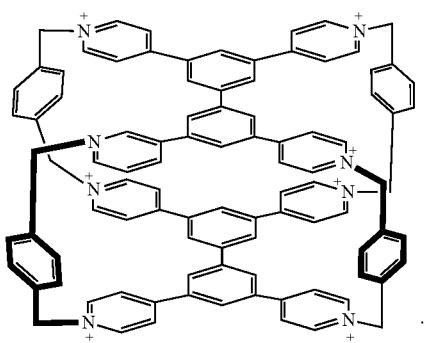

(XCage)

5. The complex of claim 3, wherein the perylene diimide dye has a formula

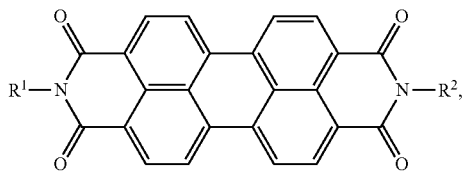

wherein $R^1$ and $R^2$ are independently selected from hydrogen, a substituted or unsubstituted, branched or unbranched, saturated or unsaturated $C_1$-$C_6$ alkyl, a substituted or unsubstituted aryl, or —OCH$_2$CH$_2$(OCH$_2$CH$_2$)$_n$—OR where R is hydrogen or a substituted or unsubstituted, branched or unbranched, saturated or unsaturated $C_1$-$C_6$ alkyl and n is an integer greater than or equal to 0.

6. The complex of claim 5, wherein R is —CH$_2$CH$_2$NMe$_2$ or —CH$_2$CH$_2$[OCH$_2$CH$_2$]$_{44}$OMe.

7. A salt comprising the cyclophane of claim 1 and a counter anion.

8. The salt of claim 7, wherein the counter anion is $CF_3CO_2^-$, $PF_6^-$, or $Cl^-$.

9. A crystalline composition comprising the complex of claim 3.

10. The crystalline composition of claim 9, wherein the crystalline composition has a triclinic, space group P-1 (no. 2) crystal parameter and wherein the crystalline composition has unit cell parameters: a=11.0±0.1, b=15.9±0.1, c=19.3±0.1 Å, α=99.2±0.1°, β=99.1±0.1°, and γ=104.4±0.1°.

11. The crystalline composition of claim 9, wherein the crystalline composition has a tetragonal, space group P4$_3$2$_1$2 crystal parameter and wherein the crystalline composition has unit cell parameters: a=40.1±0.1, and c=10.8±0.1.

* * * * *